(12) United States Patent
Renninger et al.

(10) Patent No.: US 11,046,903 B2
(45) Date of Patent: Jun. 29, 2021

(54) FUEL ADDITIVES WITH LOW NOX EMISSIONS

(71) Applicant: ExxonMobil Research and Engineering Company, Annandale, NJ (US)

(72) Inventors: Logan P. Renninger, Easton, PA (US); Scott K. Berkhous, Center Valley, PA (US); Donald J. Mattran, Spring, TX (US); Geert W. Steenbeke, Lovendegem (BE); Dongil Kang, Westfield, NJ (US); Kenneth C. H. Kar, Yardley, PA (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 0 days.

(21) Appl. No.: 16/993,850

(22) Filed: Aug. 14, 2020

(65) Prior Publication Data

US 2021/0054298 A1    Feb. 25, 2021

Related U.S. Application Data

(60) Provisional application No. 62/890,309, filed on Aug. 22, 2019.

(51) Int. Cl.
*C10L 1/23* (2006.01)
*C10L 10/12* (2006.01)
(Continued)

(52) U.S. Cl.
CPC ............ *C10L 1/231* (2013.01); *C10L 1/1824* (2013.01); *C10L 1/1852* (2013.01); *C10L 10/02* (2013.01);
(Continued)

(58) Field of Classification Search
None
See application file for complete search history.

(56) References Cited

U.S. PATENT DOCUMENTS 2,031,497 A * 2/1936 Marvel .................. C10L 1/231
                                                      44/324
2,158,050 A * 5/1939 Bereslavaky .......... C10G 59/02
                                                      44/324
(Continued)

FOREIGN PATENT DOCUMENTS

EP        0457589 A1 * 11/1991 ............. C10L 10/02
WO        9308244 A1      4/1993
WO     199308244 A1      4/1993

OTHER PUBLICATIONS

"Alkyl Nitrate Formation from the Reactions of C8-C14 n-Alkanes with OH Radicals in the Presence of NOx: Measured Yields with Essential Correction for Gas Wall Partitioning" by Geoffrey K Yeh and Paul J. Ziemann in Journal of Physical Chemistry A 2014 118, pp. 8147-8157 (Mar. 21, 2014) (Year: 2014).*

(Continued)

*Primary Examiner* — Pamela H Weiss
(74) *Attorney, Agent, or Firm* — Robert A. Migliorini

(57) ABSTRACT

This disclosure relates to compositions and methods of making an additized fuel composition comprising a base fuel composition and a randomly branched nitrate composition. The randomly branched nitrate composition includes a plurality of primary nitrate molecules, each molecule therein having an empirical chemical formula of $C_nNO_3$, wherein $C_n$ is a branched aliphatic moiety which may be the same or different for each molecule, n is an integer selected from the group consisting of 8, 9, 10, 11 and 12, at least one carbon atom in the branched aliphatic moiety being bound to three or more carbon atoms, a branching index ranging from 1.8 to 2.2, and greater than 80% of the branches in the aliphatic (Continued)

moiety being in other than the alpha position. The additized fuel composition may be diesel fuel composition or a gasoline fuel composition.

33 Claims, 20 Drawing Sheets

(51) Int. Cl.
  *C10L 10/10* (2006.01)
  *C10L 10/02* (2006.01)
  *C10L 10/14* (2006.01)
  *C10L 1/185* (2006.01)
  *C10L 1/182* (2006.01)

(52) U.S. Cl.
  CPC .............. *C10L 10/10* (2013.01); *C10L 10/12* (2013.01); *C10L 10/14* (2013.01); *C10L 2200/0423* (2013.01); *C10L 2200/0446* (2013.01); *C10L 2200/0476* (2013.01); *C10L 2200/0484* (2013.01); *C10L 2270/023* (2013.01); *C10L 2270/026* (2013.01)

(56) References Cited

U.S. PATENT DOCUMENTS

| | | | |
|---|---|---|---|
| 2,280,217 | A | 4/1942 | Cloud |
| 3,310,513 | A | 3/1967 | Barie et al. |
| 4,473,338 | A | 9/1984 | Garmong |
| 4,473,378 | A | 9/1984 | Hanlon et al. |
| 9,663,739 | B2 * | 5/2017 | Cannella ............. F02D 41/3035 |
| 10,202,929 | B1 | 2/2019 | Dec et al. |
| 2009/0320354 | A1 * | 12/2009 | Kormann ................ C10L 10/12 44/325 |
| 2010/0037513 | A1 * | 2/2010 | Petrucci .................. C10L 10/12 44/301 |
| 2014/0331953 | A1 * | 11/2014 | Cannella .................. C10L 1/23 123/1 A |

OTHER PUBLICATIONS ip.com Search History (Year: 2021).*
Dempsey, et al, "Characterization of Reactivity Controlled Compression Ignition (RCCI) Using Premixed Gasoline and Direct-Injected Gasoline With a Cetane Improver on a Multi-Cylinder Engine", 2015, vol. 8, Issue 2, pp. 859-877.
Pintor, et al, "Sensitivity for LTGC Engines: Understanding the Fundamentals and Tailoring Fuel Blends to Maximize This Property", 2019, pp. 1-24.
Hanson, et al. "An Experimental Investigation of Fuel Reactivity Controlled PCCI Combustion in a Heavy-Duty Engine", 2010, vol. 3, Issue 1, 700-717.
Yao, et al, "Progress in Energy and Combustion Science", 2009, vol. 35, pp. 398-437.
The European Search Report for EP19215889.7 dated Jun. 9, 2020.
Dempsey et al., "Characterization of Reactivity Controlled Compression Ignition (RCCI) Using Premixed Gasoline and Direct-Injected Gasoline with a Cetane Improver on a Multi-Cylinder Engine", SAE International, Apr. 14, 2015, No. 2015-01-0855, pp. 1-19.
Pintor et al., "ϕ-Sensitivity for LTGC Engines: Understanding the Fundamentals and Tailoring Fuel Blends to Maximize This Property", SAE International, Apr. 2, 2019, No. 2019-01-1961, pp. 1-24.
Hanson et al., "An Experimental Investigation of Fuel Reactivity Controlled PCCI Combustion in a Heavy-Duty Engine", SAE International, Apr. 12, 2012, No. 2010-01-1864, pp. 1-17.
Yao et al., "Progress and recent trends in homogeneous charge compression ignition (HCCI) engines", Progress in Energy and Combustion Science, Elsevier, Science Direct, 2009, No. 35, pp. 398-437.
European Search Report 19215889.7 dated Jun. 9, 2020.
Hosseini et al., "Effects of different cetane number enhancement strategies on HCCI combustion and emissions", International Journal Engine Research, NRCC, 2011 No. 12(2), pp. 89-108.
Splitter et al., "High Efficiency, Low Emissions RCCI Combustion by Use of a Fuel Additive", SAE International, Oct. 25, 2010. No. 2010-01-2167, pp. 1-15.
Wang et al., "Numerical Study of RCCI and HCCI Combustion Processes Using Gasoline, Diesel, iso-Butanol and DTBP Cetane Improver", SAE International, Apr. 14, 2015, No. 2015-01-0850, pp. 1-15.

* cited by examiner

FUEL ADDITIVES WITH LOW NOX EMISSIONS

CROSS-REFERENCE TO RELATED APPLICATIONS

This application claims priority to U.S. Provisional Application Ser. No. 62/890,309 filed Aug. 22, 2019, which is herein incorporated by reference in its entirety.

FIELD

This disclosure relates to compositions and methods for improving the ignition quality of fuels with an additive composition that has enhanced handling properties as compared to the industry standard, 2-ethylhexylnitrate (2-EHN).

BACKGROUND

Fuel ignition in diesel engines is achieved through the heat generated by air compression as a piston in the cylinder moves to reduce the cylinder volume during the compression stroke. In the engine cylinder, air is first compressed and, in doing so, heated. The fuel is then injected into the cylinder. As the fuel contacts the heated air, the self-ignition temperature of the fuel is reached and the gas vaporizes and begins to burn. Once an initial flame has been established, additional fuel is injected during the compression stroke and the newly injected fuel burns almost instantaneously. Thus, a period elapses between the beginning of fuel injection and the appearance of a flame in the cylinder. This period is commonly called "ignition delay" and should be relatively short in order to avoid "diesel knock." A major contributing factor to diesel fuel performance and the avoidance of "diesel knock" relates to the cetane number of the diesel fuel. Diesel fuels of higher cetane number exhibit a shorter ignition delay than do diesel fuels of a lower cetane number. Therefore, higher cetane number diesel fuels are desirable to avoid diesel knock. Most diesel fuels possess cetane numbers in a range of about 40 to about 55.

Cetane-improving additives have been used for many years to improve the ignition quality of diesel fuels. The use of cetane-improving additives is increasing due to the increased demand for diesel fuel. This increased demand is driven by several factors including the widening of the fraction diverted for diesel manufacture and the lowering of the natural cetane number of diesel base stocks (which is due to more severe refining of crude oil).

Fuel ignition quality also plays a critical role in operating future fleets of vehicles using low temperature combustion (LTC) engines, including homogeneous charge compression ignition (HCCI), premixed charge compression ignition (PCCI), reactivity controlled compression ignition (RCCI), and low temperature gasoline combustion (LTGC) engines. The ignition process of the LTC engines are mainly driven by fuel chemical kinetics, and the main ignition is solely relied on compression ignition without a spark plug. The LTC operation is generally achieved through premixing and dilution of fuel with either air or exhaust gas recirculation (EGR). The combustion temperature is lower than a typical diesel (compression ignition) engine, and consequently heat loss is reduced, leading to reducing NOx and soot emissions, while improving thermal efficiency. Unfortunately, however, the LTC operation is only possible for a limited engine speed and load range due to a limited range of ignition reactivity of the fuel provided. In addition, LTC combustion is sensitive to ambient temperature, making cold start a challenge.

In order for LTC strategies to be operated in a wide range of engine load conditions, fuel reactivity gradient in the engine in-cylinder is encouraged as fuel' reactivity is varied by introducing a reactivity enhancer in each operation mode.

Cetane-improving additives allow the global fuel reactivity to be varied on a cycle-to-cycle basis. In this case, a cetane-improving additive is required to be separately stored in an on-board storage system. When fuel reactivity needs to be increased, a fuel with a cetane improving additive or a cetane improving additive itself is injected, therefore, the LTC operation can be achieved over a wider range of speeds and loads. The variation in an ambient condition is compensated by appropriate use of the cetane improving additives. In this regard, the potential use of the cetane-improving additives is not necessarily restricted to diesel, but can be extended to fuels utilized in advanced combustion strategies, where the ignition reactivity of the fuel is a key enabler to achieve high-efficient and low-emission engines.

The current industry standard cetane-improving additive is 2-ethylhexylnitrate (2-EHN) for diesel fuels. Special precautions must be taken, however, when storing and handling 2-EHN due to its instability and low flash point. Further, it is believed that 2-EHN contributes to nitrogen oxide ($NO_x$) emissions derived from the combustion of the fuel, known as a fuel $NO_x$. Thus, there is a need in the art to develop alternative cetane-improving additives for diesel fuels that are safe to store and handle, especially when being stored in a separate on-board storage system of the vehicles, and have less of a negative environmental impact than 2-EHN.

SUMMARY

This disclosure relates to compositions and methods for improving the ignition quality of fuels with an additive composition that has enhanced handling properties as compared to the industry standard, 2-ethylhexylnitrate (2-EHN).

In one form of the present disclosure, provided is an additized fuel composition comprising: a base fuel composition, and a randomly branched nitrate composition comprising a plurality of primary nitrate molecules, each molecule therein having an empirical chemical formula of $C_nNO_3$, wherein $C_n$ is a branched aliphatic moiety which may be the same or different for each molecule, n is an integer selected from the group consisting of 8, 9, 10, 11 and 12, at least one carbon atom in the branched aliphatic moiety being bound to three or more carbon atoms, a branching index ranging from 1.8 to 2.2, and greater than 80% of the branches in the aliphatic moiety being in other than the alpha position; and wherein the additized fuel composition is a diesel fuel composition or a gasoline fuel composition.

In another form of the present disclosure, provided is a method for making an additized fuel composition comprising: providing a base fuel composition; and adding a randomly branched nitrate composition to the base fuel composition to form an additized fuel composition, the randomly branched nitrate composition comprising a plurality of primary nitrate molecules, each primary nitrate molecule having an empirical chemical formula of $C_nNO_3$, wherein $C_n$ is a branched aliphatic moiety which may be the same or different for each molecule, n is an integer selected from the group consisting of 8, 9, 10, 11 and 12, at least one carbon atom in the branched aliphatic moiety being bound to three or more carbon atoms, a branching index ranging from 1.8 to 2.2, and greater than 80% of the branches in the aliphatic moiety being in other than the alpha position; and wherein the additized fuel composition is a diesel fuel composition or a gasoline fuel composition.

In still another form of the present disclosure, provided is a randomly branched nitrate composition comprising a plurality of primary branched nitrate molecules having an empirical chemical formula of $C_nNO_3$, wherein $C_n$ is a branched aliphatic moiety which may be the same or different for each molecule, n is an integer selected from the group consisting of 8, 9, 10, 11 and 12, at least one carbon atom in the branched aliphatic moiety being bound to three or more carbon atoms, a branching index ranging from 1.8 to 2.2, and greater than 80% of the branches in the aliphatic moiety being in other than the alpha position. The nitrate composition of the instant disclosure may be added to a base fuel composition, wherein the base fuel composition may be a base diesel fuel or a base gasoline fuel. A resulting additized fuel composition may thus comprise a base fuel composition and a randomly branched nitrate composition, the randomly branched nitrate composition comprising a plurality of primary nitrate molecules having an empirical chemical formula of CnNO3. Cn is a branched aliphatic moiety, n is an integer greater than or equal to eight, and at least one carbon atom in the branched aliphatic moiety is bound to three or more carbon atoms.

In still yet another form of the present disclosure, provided is a method of enhancing the ignition quality of an additized gasoline fuel compositions in each engine cycle comprising: providing an additized gasoline fuel composition comprising a base gasoline fuel composition, and a randomly branched nitrate composition comprising a plurality of primary nitrate molecules, each molecule therein having an empirical chemical formula of $C_nNO_3$, wherein $C_n$ is a branched aliphatic moiety which may be the same or different for each molecule, n is an integer selected from the group consisting of 8, 9, 10, 11 and 12, at least one carbon atom in the branched aliphatic moiety being bound to three or more carbon atoms, a branching index ranging from 1.8 to 2.2, and greater than 80% of the branches in the aliphatic moiety being in other than the alpha position; and injecting the additized gasoline fuel composition into the engine to enhance ignition quality.

BRIEF DESCRIPTION OF THE DRAWINGS

The following figures are included to illustrate certain aspects of the embodiments, and should not be viewed as exclusive embodiments. The subject matter disclosed is capable of considerable modifications, alterations, combinations, and equivalents in form and function, as will occur to those skilled in the art and having the benefit of this disclosure.

DETAILED DESCRIPTION

Figure 1:
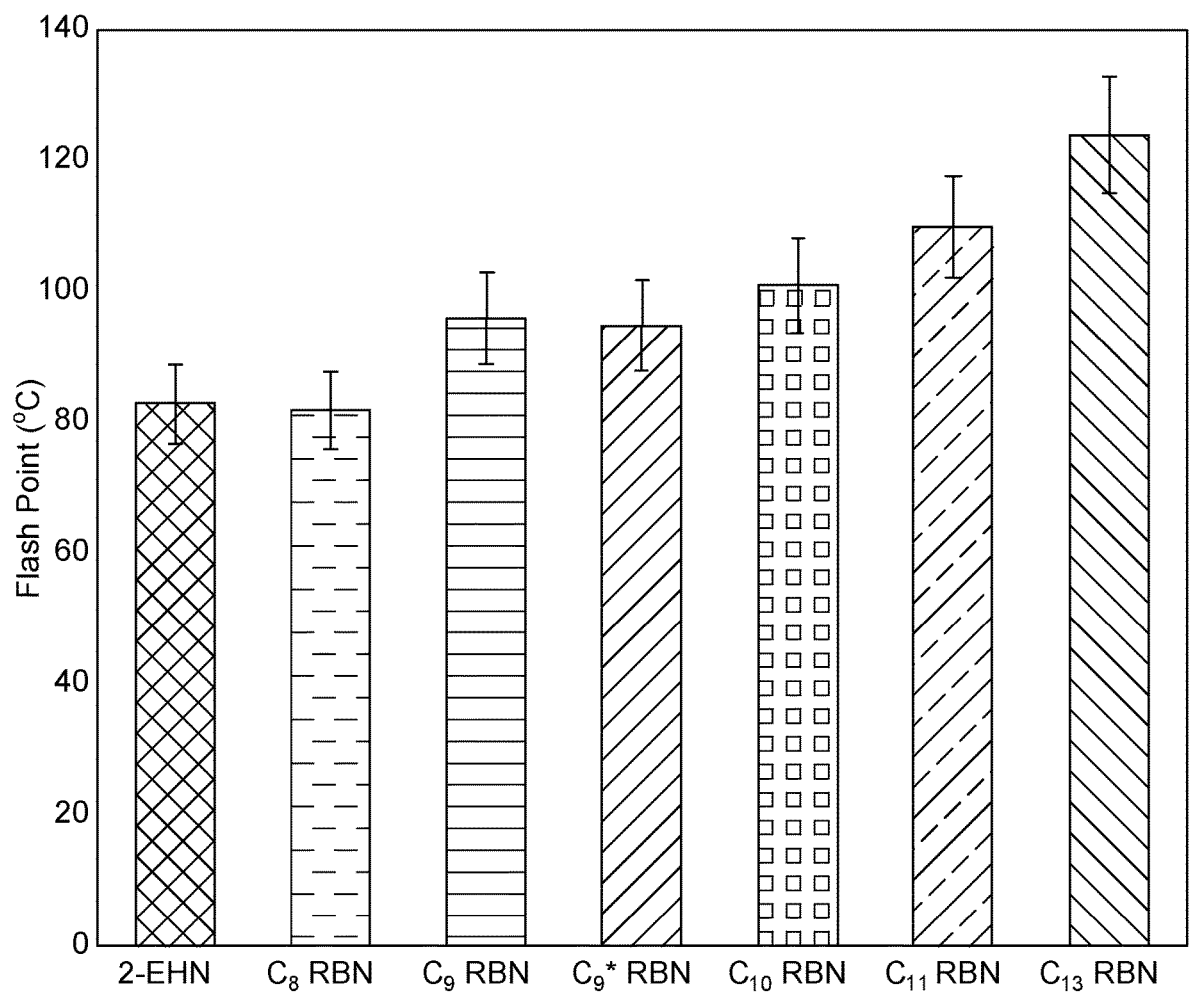
FIG. 1 provides data related to the measured flash point of samples of various embodiments of randomly branched nitrate compositions disclosed herein and as described in Example 2.

This disclosure relates to compositions and methods for improving ignition quality of diesel and gasoline fuels with an additive composition that has enhanced handling properties as compared to the industry standard, 2-ethylhexylnitrate (2-EHN).

To facilitate an understanding of the present invention, a number of terms and phrases are defined below as well as in the text following.

All numerical values within the detailed description and the claims herein are modified by "about" the indicated value, and take into account experimental error and variations that would be expected by a person having ordinary skill in the art.

As used in the present disclosure and claims, the singular forms "a," "an," and "the" include plural forms unless the context clearly dictates otherwise.

The term "and/or" as used in a phrase such as "A and/or B" herein is intended to include "A and B", "A or B," "A," and "B."

As used herein, and unless otherwise specified, the term "$C_n$," refers to a molecule having a hydrocarbon moiety with n carbon atom(s) per molecule, wherein n is a positive integer. As used herein, and unless otherwise specified, the term "$C_{n+}$" refers to a molecule having a hydrocarbon moiety with "n" or more carbon atoms, where "n" is an integer greater than 0. Similarly, the term "$C_{n-}$" refers to a molecules having a hydrocarbon moiety with "n" or fewer carbon atoms, wherein "n" is an integer greater than 0. As used herein, and unless otherwise specified, the term "$C_{n\pm x}$" refers to molecules having a hydrocarbon moiety wherein the number of carbon atoms is equal to n plus or minus x. X is an integer greater than zero. For example, if n is equal to eight, $C_{n\pm 1}$ refers to molecules having seven or nine carbon atoms.

As used herein, and unless otherwise specified, the term "aromatic" (and grammatical variations thereof) refers to unsaturated cyclic hydrocarbons having a delocalized conjugated π system and having from six to thirty carbon atoms (e.g., aromatic $C_6$-$C_{30}$ hydrocarbon).

As used herein, and unless otherwise specified, the term "aliphatic" (and grammatical variations thereof) refers to a non-aromatic moiety comprising only carbon and hydrogen atoms.

As used herein, "branched" refers to a non-cyclic aliphatic moiety containing an aliphatic linear chain or aliphatic linear backbone of carbon atoms, wherein at least one carbon atom in the linear chain is bound to three or more carbon atoms, thus creating a branch off the backbone.

As used herein, when referring to a molecule or compound, "primary" (e.g., primary nitrate, primary alcohol) refers to a moiety that is bound to a primary carbon. A primary carbon atom is a carbon atom bound to only one other carbon atom.

As used herein, when referring to the branched aliphatic moiety of the nitrate composition, a branch in the "alpha position" refers to a branch that is positioned adjacent to the carbon atom on which the alcohol group is connected. Correspondingly, when referring to the branched aliphatic moiety of the nitrate composition, a branch that is not in the alpha position refers to a branch that is not positioned adjacent to the carbon atom on which the alcohol group is connected.

As used herein, when referring to the branched aliphatic moiety, the "branching index" refers to the degree of branching as measured by the average number of branches per molecule with a higher number indicating a greater degree of branching. The branching index is measured by $^1$H NMR analysis Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. At the very least, and not as an attempt to limit the application of the doctrine of equivalents to the scope of the claim, each numerical parameter should at least be construed in light of the number of reported significant digits and by applying ordinary rounding techniques.

While compositions and methods may be described herein in terms of "comprising" various components or steps, the compositions and methods may also "consist essentially of" or "consist of" the various components and steps.

Provided herein are methods of improving the derived cetane number (DCN) of a diesel fuel composition. As used herein, derived cetane number or DCN refers to the ignition quality of a fuel. As used herein, DCN is measured and calculated using ASTM D7668-17. Ignition delays as defined in ASTM D7668 can correspond to chemical delay and physical delay. Under the method in ASTM D7668, the chemical delay can be calculated as the time required (after initial injection of fuel) for the pressure to increase to 0.2 MPa above the injection pressure. This is believed to correspond to the physical start of combustion reactions (i.e., generation of free radicals). The physical delay can be calculated based on the time between initial injection of fuel and a large rise in pressure corresponding to bulk combustion. In this discussion, the physical delay is defined as the time to reach 50% of maximum pressure in the pressure versus time curve.

Based on the chemical delay and physical delay, a correlation equation can be used to calculate the derived cetane number for a fuel composition. The correlation equation is shown in Equation (1). In Equation (1), "DCN" is derived cetane number, "CD" is the chemical delay (milliseconds), and "PD" is the physical delay (milliseconds).

$$DCN = 12.028 + \left(-\frac{5.3378}{CD}\right) + \left(\frac{300.18}{PD}\right) + \left(-\frac{1267.9}{PD^2}\right) + \left(\frac{3.415.32}{PD^3}\right) \quad (1)$$

A higher DCN indicates higher quality while a lower number indicates lower quality. As will be discussed further below, disclosed herein are methods of improving the DCN number of a base diesel fuel composition that include adding a randomly branched nitrate composition to the base diesel fuel composition.

Provided herein are also methods for improving ignition quality of gasoline fuel composition, particularly for engines operated with the advanced engine combustion concepts. Ignition reactivity of gasoline fuels can be often expressed as octane numbers (ON), research octane number (RON)

and motored octane number (MON). As used herein, RON and MON are measured using ASTM D2699 and ASTM D2700 respectively. RON in conjunction with MON defines the antiknock index of automotive spark-ignition engine fuels, in accordance with specification D4814. The antiknock index (AKI) of a fuel approximates the road octane ratings for many vehicles, is posted on retail dispensing pumps in the U.S., and is referred to in vehicle manuals.

$$AKI = \frac{(RON + MON)}{2}$$

A higher AKI indicates lower reactivity while a lower AKI indicates higher reactivity. As will be discussed further below, discussed herein are methods of improving the reactivity (decreasing the AKI number) of a base gasoline fuel composition that include adding a randomly branched nitrate composition to the base gasoline fuel composition.

Provided herein are diesel (or gasoline) fuel compositions containing a base diesel (or gasoline) fuel composition and a randomly branched nitrate composition. As used herein, a randomly branched nitrate composition refers to a composition containing mixed isomers of randomly branched primary nitrate molecules. A randomly branched nitrate composition will have a predominant fraction identifiable by the number of carbon atoms in the molecules therein. As such, a randomly branched nitrate composition may be described by the number of carbon atoms (n) in the randomly branched nitrate molecule predominant in the randomly branched nitrate composition. A randomly branched nitrate composition having predominantly randomly branched nitrate molecules with 'n' carbon atoms will be referred to herein as a "$C_n$ randomly branched nitrate composition." For example, if the majority of molecules in a randomly branched nitrate composition have eight carbon atoms, the composition will be called a $C_8$ randomly branched nitrate composition. As used herein, "branched nitrate molecule" (as well as grammatical variations thereof) refer to a molecule having an aliphatic backbone to which a nitrate moiety is attached at a primary carbon. The aliphatic backbone includes at least one carbon atom bound to three or more carbon atoms, provided that at least one carbon atom bound to three or more carbon atoms is not bound to the oxygen of the nitrate moiety. "Branch" is used herein as is commonly understood in the art as a group of atoms that connect to the longest chain of carbon atoms within the molecule at a point other than the carbon atom at the end of the chain.

A $C_n$ randomly branched nitrate composition thus contains a plurality of mixed-isomeric molecules wherein the majority having an empirical chemical formula of $C_nNO_3$ and where n is an integer from eight to thirteen. The chemical structure (I) of a branched nitrate molecule having n carbon atoms (where n is an integer) is shown below.

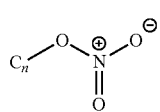

(I)

The $C_n$ moiety represents an aliphatic moiety containing an aliphatic backbone having one or more branches. The number, size, and location of the branches may be different in each molecule, creating an isomeric mixture of $C_nNO_3$ molecules, within a randomly branched nitrate composition.

A diesel fuel composition containing a randomly branched nitrate composition may have a higher derived cetane number (DCN) than the base diesel fuel composition alone.

A randomly branched nitrate composition, as described herein, may be added to a base diesel fuel composition to improve the DCN of the base diesel fuel composition. As used herein, "base diesel fuel" or "base diesel fuel composition" refers to a hydrocarbon composition having a boiling range of 140 to 370° C., or 160 to 360° C., or 180 to 350° C., or 190 to 340° C., or 200° C. to 330° C.

Base diesel fuel may include one or more of the following: hydrocarbons derived from crude oil, synthesized hydrocarbons, and biofuel. Non-limiting biofuels that may be included in the diesel or gasoline fuel compositions disclosed herein include fatty acid methyl ester, a fatty acid ethyl ester, hydrotreated vegetable oil, or blends thereof. Biofuel may comprise fatty acid methyl esters (FAME) derived from vegetable oils or animal fats (e.g., biodiesel). For example, a base fuel composition may be a blend of hydrocarbons derived from crude oil and FAME. In yet another example, a base fuel composition may be a blend of synthetic hydrocarbons and FAME. In another example, a base fuel composition may be a blend of hydrocarbons derived from crude oil, synthetic hydrocarbons, and FAME. In any base diesel or base gasoline fuel composition containing a biofuel disclosed herein, the biofuel may be present from about 1 vol. % to about 20 vol. %, including about 5 vol. %, about 10 vol. %, about 15 vol. %, from about 1 vol. % to about 5 vol. %, from about 1 vol. % to about 10 vol. %, from about 1 vol. % to about 15 vol. %, from about 5 vol. % to about 10 vol. %, from about 5 vol. % to about 15 vol. % from about 5 vol. % to about 20 vol. %, from about 10 vol. % to about 15 vol. % from about 10 vol. % to about 20 vol. %, or from about 15 vol. % to about 20 vol. %. Base diesel fuel compositions containing biofuels and in particular FAME, are used herein to illustrate the suitability of using the randomly branched nitrate compositions described herein in biodiesel-containing fuels.

A gasoline fuel composition containing a randomly branched nitrate composition may have a lower anti-knock index (AKI) than the base gasoline fuel composition alone.

A randomly branched nitrate composition, as described herein, may be added to a base gasoline fuel composition to improve the ignition reactivity of the gasoline fuel composition. As used herein, "base gasoline fuel" or "base gasoline fuel composition" refers to a hydrocarbon composition having a boiling range of 25 to 250° C. or 30 to 240° C., or 35 to 230° C., or 40 to 220° C., or 45 to 210° C., or 50 to 200'C, or 55 to 190° C., or 60 to 180° C.

A randomly branched nitrate composition, as described herein, may be added to a base diesel or base gasoline fuel composition at a concentration of up to about 500 ppmv, up to about 1000 ppmv, up to about 2000 ppmv, up to about 3000 ppmv, or up to about 4000 ppmv; ranges include from about 100 ppmv to about 500 ppmv, from about 100 ppmv to about 1000 ppmv, from about 100 ppmv to about 2000 ppmv, from about 100 ppmv to about 3000 ppmv, from about 100 ppmv to about 4000 ppmv, from about 500 ppmv to about 1000 ppmv, from about 500 ppmv to about 2000 ppmv, from about 500 ppmv to about 3000 ppmv, from about 500 ppmv to about 4000 ppmv, from about 1000 ppmv to about 2000 ppmv, from about 1000 ppmv to about 3000 ppmv, from about 1000 ppmv to about 4000 ppmv, from about 2000 ppmv to about 3000 ppmv, from about 2000 ppmv to about 4000 ppmv, and from about 3000 ppmv to about 4000 ppmv.

While the benefits of the randomly branched nitrate compositions disclosed herein will be described as being a substitute for 2-EHN, optionally, a randomly branched nitrate composition may be used in conjunction with 2-EHN to reduce the amount of 2-EHN needed for equivalent cetane improvement. Use of both 2-EHN and a randomly branched nitrate composition as described herein may thus generate a diesel fuel composition containing a base diesel fuel composition, a randomly branched nitrate composition, and 2-EHN. 2-EHN may be used at any useful concentration, such as, but not limited to, a concentration of up to about 500 ppmv, up to about 1000 ppmv, up to about 5000 ppmv, or up to about 3000 ppmv; ranges include from about 100 ppmv to about 500 ppmv, from about 100 ppmv to about 1000 ppmv, from about 100 ppmv to about 2000 ppmv, from about 100 ppmv to about 3000 ppmv, from about 500 ppmv to about 1000 ppmv, from about 500 ppmv to about 2000 ppmv, from about 500 ppmv to about 3000 ppmv, from about 1000 ppmv to about 2000 ppmv, from about 1000 ppmv to about 3000 ppmv, and from about 2000 ppmv to about 3000 ppmv of the overall diesel fuel composition.

A method of improving the cetane number of a base diesel composition (or improving reactivity of a base gasoline composition) may include providing a base diesel (or gasoline) fuel composition and adding to it a randomly branched nitrate composition and 2-EHN at concentrations described above. Alternatively, a method may include providing a diesel (or gasoline) fuel composition containing 2-EHN and adding to said composition a randomly branched nitrate composition as described herein.

As described herein, a randomly branched nitrate composition, when added to a base diesel fuel composition, may enhance the performance of the resulting diesel fuel composition similarly or better than the industry standard, 2-EHN for improving cetane in diesel fuels. For example, a diesel fuel composition containing a base diesel fuel and a randomly branched nitrate composition may have a similar or increased DCN when compared to a diesel fuel composition containing the same base diesel fuel and 2-EHN.

As described herein, a randomly branched nitrate composition, when added to a base gasoline composition, may enhance the performance of the resulting gasoline fuel composition similarly or better than 2-EHN for improving reactivity of gasoline fuels. For example, a gasoline fuel composition containing a base gasoline fuel and a randomly branched nitrate composition may have a similar or decrease RON, MON, and AKI when compared to a gasoline fuel composition containing the same base gasoline fuel and 2-EHN.

As described herein, when added to a base diesel fuel composition, it is believed that a randomly branched nitrate composition as described herein does not negatively impact the stability of the base diesel fuel to which it is added when compared to the industry standard, 2-EHN. Both 2-EHN and a randomly branched nitrate composition may reduce the oxidation induction period of the base diesel fuel composition to which it is added, which is undesirable. However, as will be described in the Examples, adding a randomly branched nitrate composition as described herein to a base diesel fuel does not reduce the oxidation induction period of the resulting diesel fuel composition more so than 2-EHN. Randomly branched nitrate compositions as described herein additionally provide the benefit of stability, as they decompose at a higher temperature than 2-EHN, and safety, as they having lower flash point than 2-EHN.

As described herein, when added to a base gasoline fuel composition, the randomly branched nitrate composition as described herein does not negatively impact the stability of the base gasoline fuel. Randomly branched nitrate compositions as described herein additionally provide the benefit of safety, as they decompose at a higher temperature than 2-EHN, and having lower flash point than 2-EHN. Therefore, a gasoline with the randomly branched nitrate would be safer to store and handle in a fuel distribution network and in a car than 2-EHN.

As described herein, when added to a base diesel fuel composition, a randomly branched nitrate composition may contribute less to nitrogen emissions (NOx) derived from fuel combustion as compared to the use of 2-EHN. For example, a C9+ randomly branched nitrate composition contains less nitrogen by weight than 2-EHN and therefore has less nitrogen available for conversion into NOx emissions. Thus, utilization of a C9+ randomly branched nitrate composition as a cetane improver may provide environmental advantages over using 2-EHN.

The additized fuel compositions disclosed herein may alternatively include one or more oxygenates. Non-limiting exemplary oxygenates include di-isopropyl ether, C5 ether, C6 ether, ethanol, methanol, propanol, 2-propanol, butanol, 2-butanol, iso-butanol, tert-butanol, and mixtures thereof. The one or more oxygenates may be included in the additized fuel compositions disclosed herein at from 0.1 to 20 vol. %, or 0.5 to 18 vol. %, or 1 to 16 vol. %, or 2 to 14 vol. %, 3 to 12 vol. %, or 4 to 10 vol. %, or 5 to 8 vol. %, or 6 to 7 vol. %.

Properties and Preparation of Randomly Branched Nitrate Compositions

The randomly branched nitrate composition of the instant disclosure includes a plurality of primary nitrate molecules with each primary nitrate molecule having an empirical chemical formula of $C_nNO_3$, wherein $C_n$ is a branched aliphatic moiety which may be the same or different for each molecule, and n is an integer selected from the group consisting of 8, 9, 10, 11 and 12. Alternatively, n is an integer selected from the group consisting of 9, 10, and 11. Alternatively n may be 9. Still alternatively n may be 10. Still further alternatively n may be 11.

A particular $C_n$ randomly branched nitrate composition may comprise at least about 75 wt. %, at least about 80 wt. %, at least about 85 wt. %, at least about 90 wt. %, at least about 95 wt. %, at least about 99 wt. % or about 100 wt. % of $C_n$ randomly branched nitrate molecules; ranges include about 75 wt. % to about 100 wt. %, about 80 wt. % to about 100 wt. %, about 85 wt. % to about 100 wt. %, about 90 wt. % to about 100 wt. %, about 95 wt. % to about 100 wt. %, about 75 wt. % to about 95 wt. %, about 80 wt. % to about 95 wt. %, about 85 wt. % to about 95 wt. %, about 90 wt. % to about 95 wt. %, about 85 wt. % to about 95 wt. %, or about 90 wt. % to about 95 wt. % of $C_n$ randomly branched nitrate molecules. A particular $C_n$ randomly branched nitrate composition may comprise a plurality of randomly branched nitrate molecules with n±1 carbon atoms ($C_{n±1}$ randomly branched nitrate molecules). For example, a $C_8$ randomly branched nitrate composition may comprise a plurality of $C_7$ and/or $C_9$ randomly branched nitrate molecules.

A particular $C_n$ randomly branched nitrate composition may comprise up to about 25 wt. %, up to about 20 wt. %, up to about 15 wt. %, up to about 10 wt. %, up to about 5 wt. %, or the $C_n$ randomly branched nitrate composition may be substantially absent $C_{n±1}$ randomly branched nitrate molecules. Suitable ranges include about 0 wt. % to about 25 wt. %, about 0 wt. % to about 20 wt. %, about 0 wt. % to about 15 wt. %, about 0 wt. % to about 10 wt. %, about 0 wt. % to about 5 wt. %, about 5 wt. % to about 25 wt. %, about 5 wt. % to about 20 wt. %, about 5 wt. % to about 15 wt. %, about 5 wt. % to about 10 wt. %, about 10 wt. % to about 25 wt. %, about 10 wt. % to about 20 wt. %, about 10 wt. % to about 15 wt. %, about 15 wt. % to about 25 wt. %, about 15 wt. % to about 20 wt. %, and about 20 wt. % to about 25 wt. % of $C_{n+1}$ randomly branched nitrate molecules. A particular $C_n$ randomly branched nitrate composition may contain a plurality of randomly branched nitrate molecules having n±2 carbon atoms ($C_{n+2}$ randomly branched nitrate molecules). For example, a $C_8$ randomly branched nitrate composition may comprise a plurality of $C_6$ and/or $C_{10}$ randomly branched nitrate molecules. A particular $C_n$ randomly branched nitrate composition may contain up to about 25 wt. %, up to about 20 wt. %, up to about 15 wt. %, up to about 10 wt. %, up to about 5 wt. %, or the $C_n$ randomly branched nitrate composition may be substantially absent $C_{n+2}$ randomly branched nitrate molecules. Suitable ranges include about 0 wt. % to about 25 wt. %, about 0 wt. % to about 20 wt. %, about 0 wt. % to about 15 wt. %, about 0 wt. % to about 10 wt. %, about 0 wt. % to about 5 wt. %, about 5 wt. % to about 25 wt. %, about 5 wt. % to about 20 wt. %, about 5 wt. % to about 15 wt. %, about 5 wt. % to about 10 wt. %, about 10 wt. % to about 25 wt. %, about 10 wt. % to about 20 wt. %, about 10 wt. % to about 15 wt. %, about 15 wt. % to about 25 wt. %, about 15 wt. % to about 20 wt. %, and about 20 wt. % to about 25 wt. % $C_{n+2}$ randomly branched nitrate molecules. A particular $C_n$ randomly branched nitrate composition may comprise a plurality of randomly branched nitrate molecules where the number of carbon atoms is equal to or less than four ($C_{4-}$ randomly branched nitrate molecules). A particular $C_n$ randomly branched nitrate composition may comprise up to about 5 wt. %, up to about 4 wt. %, up to about 3 wt. %, up to about 2 wt. %, up to about 1 wt. %, up to about 0.5 wt. %, or the $C_n$ randomly branched nitrate composition may be substantially absent $C_{4-}$ randomly branched nitrate molecules. Suitable ranges include about 0 wt. % to about 5 wt. %, about 0 wt. % to about 4 wt. %, about 0 wt. % to about 3 wt. %, about 0 wt. % to about 2 wt. %, about 0 wt. % to about 1 wt. %, about 0 wt. % to about 0.5 wt. %, about 0.5 wt. % to about 5 wt. %, about 0.5 wt. % to about 4 wt. %, about 0.5 wt. % to about 3 wt. %, about 0.5 wt. % to about 2 wt. %, about 0.5 wt. % to about 1 wt. %, about 1 wt. % to about 5 wt. %, about 1 wt. % to about 4 wt. %, about 1 wt. % to about 3 wt. %, about 1 wt. % to about 2 wt. %, about 2 wt. % to about 5 wt. %, about 2 wt. % to about 4 wt. %, about 2 wt. % to about 3 wt. %, about 3 wt. % to about 5 wt. %, about 3 wt. % to about 4 wt. %, and about 4 wt. % to about 5 wt. % of $C_{4-}$ randomly branched nitrate molecules. In any embodiment, a G randomly branched nitrate composition may contain up to about 25 wt. % of randomly branched nitrate molecules wherein each branched nitrate molecule has an aliphatic moiety with more or less than 'n' carbon atoms (e.g., n±1 carbon atoms).

In any embodiment, a $C_n$ randomly branched nitrate composition may contain a variety of branched nitrate isomers (including isomers of $C_n$, $C_{n+1}$, and $C_{n\pm2}$ molecules therein). In any randomly branched nitrate composition, the branch position, length, and number of branches may vary from molecule to molecule therein. For example, a branched nitrate molecule within a randomly branched nitrate composition may contain one or more branches having one or more carbon atoms positioned anywhere along the aliphatic carbon backbone (except $C_1$). One of skill in the art would be able to envisage the limited number of isomers possible in any given branched nitrate molecule.

In an example embodiment of a randomly branched nitrate composition, the average number of branches per molecule (also referred to as the branching index as defined above) is from about 1.5 branches per branched nitrate molecule to about 3.5 branches per branched nitrate molecule. Preferably, branched nitrate molecules in a $C_8$ randomly branched nitrate composition include, on average, about 1.6 branches per molecule. Preferably, branched nitrate molecules in a $C_9$ randomly branched nitrate composition (including $C_9^*$) include, on average, about 1.8 branches per molecule. Preferably, branched nitrate molecules in a $C_{10}$ randomly branched nitrate composition include, on average, about 2.0 branches per molecule. Preferably, branched nitrate molecules in a $C_{11}$ randomly branched nitrate composition include, on average, about 2.2 branches per molecule. Preferably, the branched nitrate molecules in a $C_{13}$ randomly branched nitrate composition include, on average, about 3.1 branches per molecule. The branching index may also range from 1.5 to 3.0, or 1.6 to 2.9, or 1.7 to 2.8, or 1.8 to 2.7, or 1.9 to 2.6, or 2.0 to 2.5, or 2.1 to 2.4, or 2.2 to 2.3.

In an example embodiment of a randomly branched nitrate composition, for the branching in the aliphatic moiety, greater than 60%, or greater than 70%, or greater than 80%, or greater than 90% of the branches in the aliphatic moiety are in other than the alpha position as measured by $^{13}$C NMR analysis of branching.

A majority of nitrate molecules in a $C_n$ randomly branched nitrate composition suitable for the methods are branched. For example, greater than about 90 wt. % of molecules in a $C_n$ randomly branched nitrate composition may be branched, including greater than about 92 wt. %, greater than about 95 wt. %, greater than about 97 wt. %, greater than about 99 wt. %, or substantially 100 wt. % may be branched. This includes from about 90 wt. % to substantially 100 wt. %, from about 92 wt. % to substantially 100 wt. %, from about 95 wt. % to substantially 100 wt. % from about 97 wt. % to substantially 100 wt. %, from about 99 wt. % to substantially 100 wt. %, from about 90 wt. % to about 99 wt. %, from about 90 wt. % to about 97 wt. %, from about 90 wt. % to about 95 wt. %, from about 90 wt. % to about 92 wt. %, from about 92 wt. % to about 99 wt. %, from about 92 wt. % to about 97 wt. %, from about 92 wt. % to about 95 wt. %, from about 95 wt. % to about 99 wt. %, from about 95 wt. % to about 97 wt. %, and from about 97 wt. % to about 99 wt. % of nitrate molecules in a $C_n$ randomly branched nitrate composition. In any embodiment, a G randomly branched nitrate composition may optionally contain some linear or normal nitrate molecules. For example, a $C_n$ randomly branched nitrate composition may contain from substantially 0 wt. % to about 10 wt. % linear or normal G nitrate molecules.

In any embodiment, a $C_n$ randomly branched nitrate composition may comprise a dominant isomer and/or a dominant branch size. For example, the majority of branched nitrate molecules in a $C_n$ randomly branched nitrate composition may have methyl branches. In a particular example, a majority of branched nitrate molecules in a $C_n$ randomly branched nitrate composition may have one, two, or three methyl branches. For example, a $C_n$ randomly branched nitrate composition may comprise at least about 75 wt. %, at least about 80 wt. %, at least about 85 wt. %, at least about 90 wt. %, at least about 95 wt. %, at least about 99 wt. % or about 100 wt. % of randomly branched nitrate molecules having have one, two, or three methyl branches; ranges include about 75 wt. % to about 100 wt. %, about 80 wt. % to about 100 wt. %, about 85 wt. % to about 100 wt. %, about 90 wt. % to about 100 wt. %, about 95 wt. % to about 100 wt. %, about 75 wt. % to about 95 wt. %, about 80 wt. % to about 95 wt. %, about 85 wt. % to about 95 wt. %, about 90 wt. % to about 95 wt. %, about 85 wt. % to about 95 wt. %, or about 90 wt. % to about 95 wt. % of $C_n$ randomly branched nitrate molecules wherein each branched nitrate molecule has one, two, or three methyl branches.

A $C_n$ randomly branched nitrate composition may be prepared, for example, by nitration (e.g., with nitric acid and a nitric acid activating compound) of composition comprising a plurality of $C_n$ branched primary alcohol molecules. For example, a composition of $C_n$ branched alcohol molecules may be subjected to nitration to form a composition of $C_n$ branched nitrate molecules. Once prepared, if desired, a $C_n$ branched nitrate composition may be combined with one or more $C_n$ branched nitrate compositions, where n of each of the one or more $C_n$ branched nitrate compositions is different from n of the first $C_n$ branched nitrate composition. In this way, a $C_n$ randomly branched nitrate composition may be generated. In another example, a $C_n$ randomly branched nitrate composition may be prepared by converting a plurality of mixed isomer randomly branched primary alcohol molecules in a $C_n$ randomly branched alcohol composition (e.g., such as those sold under the tradename EXXAL™ by Exxon Mobil) to a plurality of $C_n$ randomly branched mixed isomer nitrate molecules to generate a $C_n$ randomly branched nitrate composition. As used herein, the majority of the branched primary alcohol molecules in a $C_n$ branched alcohol composition have an empirical formula of $C_n OH$, wherein n is an integer of at least eight (e.g., from eight to thirteen).

As such, a $C_n$ randomly branched alcohol composition may comprise at least about 75 wt. %, at least about 80 wt. %, at least about 85 wt. %, at least about 90 wt. %, at least about 95 wt. %, at least about 99 wt. % or about 100 wt. % of $C_n$ randomly branched alcohol molecules; ranges include about 75 wt. % to about 100 wt. %, about 80 wt. % to about 100 wt. %, about 85 wt. % to about 100 wt. %, about 90 wt. % to about 100 wt. %, about 95 wt. % to about 100 wt. %, about 75 wt. % to about 95 wt. %, about 80 wt. % to about 95 wt. %, about 85 wt. % to about 95 wt. %, about 90 wt. % to about 95 wt. %, about 85 wt. % to about 95 wt. %, or about 90 wt. % to about 95 wt. % of $C_n$ randomly branched alcohol molecules. A particular $C_n$ randomly branched alcohol composition may comprise a plurality of randomly branched alcohol molecules having n±1 carbon atoms ($C_{n\pm1}$ randomly branched alcohol molecules). For example, a $C_8$ randomly branched alcohol composition may comprise a plurality of $C_7$ and/or $C_9$ randomly branched alcohol molecules. A particular $C_n$ randomly branched alcohol composition may comprise up to about 25 wt. %, up to about 20 wt. %, up to about 15 wt. %, up to about 10 wt. %, up to about 5 wt. %, or the $C_n$ randomly branched alcohol composition may be substantially absent $C_{n\pm1}$ randomly branched alcohol molecules. Suitable ranges include about 0 wt. % to about 25 wt. %, about 0 wt. % to about 20 wt. %, about 0 wt. % to about 15 wt. %, about 0 wt. % to about 10 wt. %, about 0 wt. % to about 5 wt. %, about 5 wt. % to about 25 wt. %, about 5 wt. % to about 20 wt. %, about 5 wt. % to about 15 wt. %, about 5 wt. % to about 10 wt. %, about 10 wt. % to about 25 wt. %, about 10 wt. % to about 20 wt. %, about 10 wt. % to about 15 wt. %, about 15 wt. % to about 25 wt. %, about 15 wt. % to about 20 wt. %, and about 20 wt. % to about 25 wt. % of $C_{n\pm1}$ randomly branched alcohol molecules. A particular $C_n$ randomly branched alcohol composition may comprise a plurality of randomly branched alcohol molecules having n±2 carbon atoms ($C_{n\pm2}$ randomly branched alcohol molecules). For example, a $C_8$ randomly branched alcohol composition may comprise a plurality of $C_6$ and/or $C_{10}$ randomly branched alcohol molecules. A particular $C_n$ randomly branched alcohol composition may comprise up to about 25 wt. %, up to about 20 wt. %, up to about 15 wt. %, up to about 10 wt. %, up to about 5 wt. % of $C_{n\pm2}$ randomly branched alcohol molecules, or the $C_n$ randomly branched alcohol composition may be substantially absent $C_{n\pm2}$ randomly branched alcohol molecules. Suitable ranges include about 0 wt. % to about 25 wt. %, about 0 wt. % to about 20 wt. %, about 0 wt. % to about 15 wt. %, about 0 wt. % to about 10 wt. %, about 0 wt. % to about 5 wt. %, about 5 wt. % to about 25 wt. %, about 5 wt. % to about 20 wt. %, about 5 wt. % to about 15 wt. %, about 5 wt. % to about 10 wt. %, about 10 wt. % to about 25 wt. %, about 10 wt. % to about 20 wt. %, about 10 wt. % to about 15 wt. %, about 15 wt. % to about 25 wt. %, about 15 wt. % to about 20 wt. %, and about 20 wt. % to about 25 wt. % of $C_{n\pm2}$ randomly branched alcohol molecules. A particular $C_n$ randomly branched alcohol composition may comprise a plurality of randomly branched alcohol molecules where the number of carbon atoms in the molecule is equal to or less than four ($C_{4-}$ randomly branched alcohol molecules). A particular $C_n$ randomly branched alcohol composition may comprise up to about 5 wt. %, up to about 4 wt. %, up to about 3 wt. %, up to about 2 wt. %, up to about 1 wt. %, up to about 0.5 wt. %, or the $C_n$ randomly branched alcohol composition may be substantially absent $C_{4-}$ randomly branched alcohol molecules (i.e., about 0 wt. %). Suitable ranges include about 0 wt. % to about 5 wt. %, about 0 wt. % to about 4 wt. %, about 0 wt. % to about 3 wt. %, about 0 wt. % to about 2 wt. %, about 0 wt. % to about 1 wt. %, about 0 wt. % to about 0.5 wt. %, about 0.5 wt. % to about 5 wt. %, about 0.5 wt. % to about 4 wt. %, about 0.5 wt. % to about 3 wt. %, about 0.5 wt. % to about 2 wt. %, about 0.5 wt. % to about 1 wt. %, about 1 wt. % to about 5 wt. %, about 1 wt. % to about 4 wt. %, about 1 wt. % to about 3 wt. %, about 1 wt. % to about 2 wt. %, about 2 wt. % to about 5 wt. %, about 2 wt. % to about 4 wt. %, about 2 wt. % to about 3 wt. %, about 3 wt. % to about 5 wt. %, about 3 wt. % to about 4 wt. %, and about 4 wt. % to about 5 wt. % of $C_{4-}$ randomly branched alcohol molecules. In any embodiment, the concentration of randomly branched alcohol molecules having more or fewer carbon atoms than 'n' in a $C_n$ randomly branched nitrate composition may be up to about 25 wt. % (i.e., from about 0 wt. % to about 25 wt. %).

In any embodiment, a $C_n$ randomly branched alcohol composition may include a variety of isomers. For example, in any given branched alcohol molecule having one or more branches, the one or more branches may vary in length and branch point off the aliphatic backbone (with the exception of the $C_1$ position, which does not have a branch). In any $C_n$ randomly branched alcohol composition, a molecule therein may contain one or more branches having one or more carbon atoms. One of skill in the art will readily be able to envisage the limited number of isomers possible in any given branched alcohol molecule. The average number of branches per molecule of a $C_n$ randomly branched alcohol composition may be from about 1.5 branches per branched alcohol molecule to about 3.5 branches per branched alcohol molecule. For example, in any embodiment, randomly branched alcohol molecules in a $C_8$ randomly branched alcohol composition may have about 1.6 branches per molecule. In any embodiment, randomly branched alcohol molecules in a $C_9$ randomly branched alcohol composition (or $C_9$*randomly branched alcohol composition) may have, on average, about 1.8 branches per molecule. In any embodiment, randomly branched alcohol molecules in a Cm randomly branched alcohol composition may have, on average, about 2.0 branches per molecule. In any embodiment, randomly branched alcohol molecules in a $C_{11}$ randomly branched alcohol composition may have, on average, about 2.2 branches per molecule. In any embodiment, randomly branched alcohol molecules in a $C_{13}$ randomly branched alcohol composition may have, on average, about 3.1 branches per molecule.

Alternatively, a $C_n$ randomly branched alcohol composition may comprise a dominant $C_n$ isomer and/or a dominant branch size. For example, the majority of molecules in a $C_n$ randomly branched alcohol composition may have methyl branches. In a particular example, a majority of branched alcohol molecules in a $C_n$ randomly branched alcohol composition may have one methyl branch or two methyl branches. For example, a $C_n$ randomly branched alcohol composition may comprise at least about 75 wt. %, at least about 80 wt. %, at least about 85 wt. %, at least about 90 wt. %, at least about 95 wt. %, at least about 99 wt. % or about 100 wt. % of randomly branched alcohol molecules with one, two, or three methyl branches; ranges include about 75 wt. % to about 100 wt. %, about 80 wt. % to about 100 wt. %, about 85 wt. % to about 100 wt. %, about 90 wt. % to about 100 wt. %, about 95 wt. % to about 100 wt. %, about 75 wt. % to about 95 wt. %, about 80 wt. % to about 95 wt. %, about 85 wt. % to about 95 wt. %, about 90 wt. % to about 95 wt. %, about 85 wt. % to about 95 wt. %, or about 90 wt. % to about 95 wt. % of randomly branched alcohol molecules having one, two, or three methyl branches.

A $C_n$ randomly branched alcohol composition may be prepared by methods well known in the art, for example, by hydroformylation of olefins followed by hydrogenation of the aldehyde or by polymerization of lower alkenes (e.g., $C_2$-$C_4$ alkenes) followed by hydration of the resulting olefin. In any embodiment, a composition containing randomly branched alcohol molecules may be purified to isolate a particular fraction (e.g., a fraction having a desired value or range of values of n), by methods well known in the art (e.g., by distillation).

As discussed in the Background, caution should be taken in the storage and handling of 2-EHN. Advantageously, a randomly branched nitrate composition as described herein may be safer to store and to handle than 2-EHN. For example, a randomly branched nitrate composition prepared by the methods disclosed herein may have a higher flash point than 2-EHN (which is about 76° C.), and thus be less susceptible to auto-ignition at a given temperature. Flash point may be measured according to ASTM D93-18. For example, a randomly branched nitrate composition may have a flash point greater than about 76° C., greater than about 80° C., greater than about 90° C., greater than about 100° C., greater than about 110° C., or greater than about 120° C.; ranges include from about 80° C. to about 140° C., from about 80° C. to about 120° C., from about 80° C. to about 110° C., from about 80° C. to about 100° C., from about 80° C. to about 90° C., from about 90° C. to about 140° C., from about 90° C. to about 120° C., from about 90° C. to about 110° C., from about 90° C. to about 100° C., from about 100° C. to about 140° C., from about 100° C. to about 120° C., from about 100° C. to about 110° C., from about 110° C. to about 140° C., from about 110° C. to about 120° C., or from about 120° C. to about 140° C.

In another example, a randomly branched nitrate composition prepared by methods disclosed herein may have a higher thermal degradation temperature than 2-EHN (which is about 125° C.), similarly indicating a reduced susceptibility to auto-ignition. Thermal degradation may be measured by thermal gravimetric analysis (TGA). For example, a randomly branched nitrate composition may have a thermal degradation temperature of greater than about 125° C., greater than about 135° C., greater than about 145° C., greater than about 155° C., greater than about 165° C., greater than about 175° C., greater than about 185° C., greater than about 195° C., or greater than about 205° C.; ranges include about 130° C. to about 205° C., about 130° C. to about 205° C., about 130° C. to about 195° C., about 130° C. to about 185° C., about 130° C. to about 175° C., about 130° C. to about 165° C., about 130° C. to about 155° C., about 130° C. to about 145° C., about 130° C. to about 135° C., about 135° C. to about 205° C., about 135° C. to about 195° C., about 135° C. to about 185° C., about 135° C. to about 175° C., about 135° C. to about 165° C., about 135° C. to about 155° C., about 135° C. to about 145° C., about 145° C. to about 205° C., about 145° C. to about 195° C., about 145° C. to about 185° C., about 145° C. to about 175° C., about 145° C. to about 165° C., about 145° C. to about 155° C., about 155° C. to about 205° C., about 155° C. to about 195° C., about 155° C. to about 185° C., about 155° C. to about 175° C., about 155° C. to about 165° C., about 165° C. to about 205° C., about 165° C. to about 195° C., about 165° C. to about 185° C., about 165° C. to about 175° C., about 175° C. to about 205° C., about 175° C. to about 195° C., about 175° C. to about 185° C., about 185° C. to about 205° C., about 185° C. to about 195° C., or about 195° C. to about 205° C.

Storage of a diesel fuel composition may result in oxidation and degradation of the fuel and the formation of sediment. Advantageously, when compared to using 2-EHN, a randomly branched nitrate composition prepared by methods disclosed herein may not impact the rate of natural oxidation and/or degradation of the diesel fuel composition to which it is added more so than 2-EHN, particularly when used at lower concentrations (e.g., less than about 2000 ppmv). Oxidation and degradation of a diesel fuel may be measured, for example, by ASTM D4625-16e1. For example, in any embodiment, a sample of diesel fuel containing a randomly branched nitrate composition as disclosed herein may contain less than about 2 mg sediment per 100 mL of diesel fuel, or from about 0 mg/100 mL to about 2 mg/100 mL, from about 0 mg/100 mL to about 1.5 mg/100 mL, or from about 0 mg/100 mL to about 1.0 mg/100 mL after storage for six weeks at 43° C.

Storage of a randomly branched nitrate composition prepared by methods disclosed herein is advantageous over 2-EHN. For vehicles using LTC concepts which requires storing cetane improving additives onboard, a randomly branched nitrate composition would offer a safer handling and storage due to the higher flash point and decomposition temperature than 2-EHN.

For vehicle using LTC concepts, a couple of different approaches of introducing a randomly branched nitrate composition to the combustion process may be considered. First, the amounts of the cetane improving additives are separately stored in on-board storage, selectively introduced to the fuel injection system, and mixed with the base fuel before injected into the engine in-cylinder. Secondly, a cetane improving additive can be separately stored in on-board storage and directly injected into the engine in-cylinder separately from the base fuel. Lastly, a base fuel mixed with cetane improving additives can be separately stored in on-board storage and directly injected into the engine in-cylinder separately from the base fuel.

The randomly branched nitrate compositions disclosed herein having greater than eight carbon atoms disclosed herein have a lower nitrogen content per molecule than the industry standard, 2-EHN. Nitrogen content is environmentally relevant as fuel-derived nitrogen (e.g., the nitrogen in the randomly branched nitrate molecules) contributes to nitrogen oxide ($NO_x$) emissions and pollution of the environment. As used herein, $NO_x$ refers to nitrogen oxide compounds, including NO and $NO_2$. $NO_x$ pollution causes respiratory issues and damages ecosystems. Reducing the nitrogen content in the fuel by reducing the nitrogen content of fuel additives will, in turn, reduce $NO_x$ emissions.

One or more illustrative embodiments incorporating the invention embodiments disclosed herein are presented herein. Not all features of a physical implementation are described or shown in this application for the sake of clarity. It is understood that in the development of a physical embodiment incorporating the embodiments of the present invention, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for those of ordinary skill in the art and having benefit of this disclosure.

EXAMPLE EMBODIMENTS

One nonlimiting example embodiment is a diesel fuel composition comprising a base diesel fuel composition and a randomly branched nitrate composition comprising a plurality of primary nitrate molecules, each molecule having an empirical chemical formula of $C_nNO_3$, wherein $C_n$ is a branched aliphatic moiety, n is an integer greater than or equal to eight, and at least one carbon atom in the branched aliphatic moiety is bound to three or more carbon atoms. Optionally, the embodiment may further include one or more of the following Elements: Element 1: the diesel fuel composition wherein the base diesel fuel composition comprises a biofuel; Element 2: the diesel fuel composition wherein the base diesel fuel composition comprises a fatty acid methyl ester, a fatty acid ethyl ester, hydrotreated vegetable oil, or a blend thereof; Element 3: the diesel fuel composition wherein n is 8, 9, 10, 11, 12, or 13; Element 4: the diesel fuel composition wherein the concentration of $C_nNO_3$ molecules in the randomly branched nitrate composition is at least about 60 wt. %; Element 5: the diesel fuel composition wherein the concentration of $C_nNO_3$ molecules in the randomly branched nitrate composition is at least about 60 wt. % and less than about 98 wt. %; Element 6: the diesel fuel composition wherein one of the carbon atoms bound to the at least one carbon atom in the branched is part of a methyl group; Element 7: the diesel fuel composition wherein the randomly branched nitrate composition further comprises: a primary nitrate molecule having an empirical chemical formula of $C_{n-1}NO_3$, wherein $C_{n-1}$ is a branched aliphatic moiety, n is an integer greater than or equal to eight, and at least one carbon atom in the branched aliphatic moiety is bound to three or more carbon atoms; and a primary nitrate molecule having an empirical chemical formula of $C_{n+1}NO_3$, wherein $C_{n+1}$ is a branched aliphatic moiety, n is an integer greater than or equal to eight, and at least one carbon atom in the branched aliphatic moiety is bound to three or more carbon atoms; Element 8: the diesel fuel composition wherein the randomly branched nitrate composition is present at a concentration of about 500 ppmv to about 4000 ppmv; Element 9: the diesel fuel composition wherein the randomly branched nitrate composition is present at a concentration of about 500 ppmv to about 2000 ppmv; Element 10: the diesel fuel composition wherein when said diesel fuel composition is combusted in the presence of oxygen, a lower mass of nitrogen oxide and nitrogen dioxide is produced than the mass of nitrogen oxide and nitrogen dioxide produced from the combustion of a diesel fuel composition comprising the base diesel fuel composition and a concentration of 2-ethylhexyl nitrate equal to the concentration of the randomly branched nitrate composition in the diesel fuel composition; and Element 11: the diesel fuel composition wherein after storage of the diesel fuel composition comprising about 1000 ppmv of the randomly branched nitrate composition for about six weeks at about 43° C., the diesel fuel composition comprises less than about 1.0 mg/100 mL of insoluble material as measured according to ASTM D4625-16e1; and Element 34: the diesel fuel composition, further comprising 2-EHN. Examples of combinations include, but are not limited to, Element 1 in combination with one or more of Elements 2-11 and 34; Element 2 in combination with one or more of Elements 3-11 and 34; Element 3 in combination with one or more of Elements 4-11 and 34; Element 4 in combination with one or more of Elements 5-11 and 34; Element 5 in combination with one or more of Elements 6-11 and 34; Element 6 in combination with one or more of Elements 7-11 and 34; Element 7 in combination with one or more of Elements 8-11 and 34; Element 8 in combination with one or more of Elements 9-11 and 34; Element 9 in combination with one or both of Elements 10-11 and 34; Element 10 in combination with one or more of Elements 11 and 34; and Element 11 in combination with Element 34.

Another nonlimiting example embodiment is a method comprising: adding a randomly branched nitrate composition to a base diesel fuel composition to form an additized diesel fuel composition, the randomly branched nitrate composition comprising a plurality of primary nitrate molecules, each primary nitrate molecule having an empirical chemical formula of $C_nNO_3$, wherein $C_n$ is a branched aliphatic moiety, n is an integer greater than or equal to eight, and at least one carbon atom in the branched aliphatic moiety is bound to three or more carbon atoms. Optionally, the embodiment may further include one or more of the following Elements: Element 12: the method wherein the base diesel fuel composition comprises a biofuel; Element 13: the method wherein the base diesel fuel composition comprises a fatty acid methyl ester, a fatty acid ethyl ester, hydrotreated vegetable oil, or a blend thereof; Element 14: the method wherein n is 8, 9, 10, 11, 12, or 13; Element 15: the method wherein the concentration of $C_nNO_3$ molecules in the randomly branched nitrate composition is at least about 60 wt. %; Element 16: the method wherein the concentration of $C_nNO_3$ molecules in the randomly branched nitrate composition is at least about 60 wt. % and less than about 98 wt. %; Element 17: the method wherein substantially all the primary nitrate molecules in the randomly branched nitrate composition have at least one carbon atom in the branched aliphatic moiety is bound to three or more carbon atoms; Element 18: the method wherein the randomly branched nitrate composition further comprises a primary branched nitrate molecule having an empirical chemical formula of $C_{n-1}NO_3$, wherein $C_{n-1}$ is a branched aliphatic moiety, n is an integer greater than or equal to eight, and at least one carbon atom in the branched aliphatic moiety is bound to three or more carbon atoms; and a primary branched nitrate molecule having an empirical chemical formula of $C_{n+1}NO_3$, wherein $C_{n+1}$ is a branched aliphatic moiety, n is an integer greater than or equal to eight, and at least one carbon atom in the branched aliphatic moiety is bound to three or more carbon atoms; Element 19: the method wherein one of the carbon atoms bound to the at least one carbon atom in the branched is part of a methyl group; Element 20: the method wherein the diesel fuel composition comprises the randomly branched nitrate composition at a concentration of about 100 ppmv to about 4000 ppmv; Element 21: the method wherein the diesel fuel composition comprises the randomly branched nitrate composition at a concentration of about 100 ppmv to about 2000 ppmv; Element 22: the method wherein the randomly branched nitrate composition is characterized by a flash point of about 80° C. or greater; Element 23: the method wherein the diesel fuel composition has a higher derived cetane number than the base diesel fuel composition; Element 24: the method wherein the derived cetane number of the diesel fuel composition is greater than the derived cetane number of the base diesel fuel composition by at least about 4; Element 25: the method wherein the diesel fuel composition has a higher derived cetane number than the base diesel fuel composition; Element 26: the method wherein the randomly branched nitrate composition is characterized by a flash point of about 80° C. or greater; Element 27: the method wherein the additized diesel fuel composition is supplied to a gas station; and Element 28; the method wherein the base diesel fuel composition comprises a biofuel. Example combinations include, but are not limited to, Element 12 in combination with one or more of Elements 13-28; Element 13 in combination with one or more of Elements 14-28; Element 14 in combination with one or more of Elements 15-28; Element 15 in combination with one or more of Elements 16-28; Element 16 in combination with one or more of Elements 17-28; Element 17 in combination with one or more of Elements 18-28; Element 18 in combination with one or more of Elements 19-28; Element 19 in combination with one or more of Elements 20-28; Element 20 in combination with one or more of Elements 21-28; Element 21 in combination with one or more of Elements 22-28; Element 22 in combination with one or more of Elements 23-28; Element 23 in combination with one or more of Elements 24-28; Element 24 in combination with one or more of Elements 25-28; Element 25 in combination with one or more of Elements 26-28; Element 26 in combination with one or both of Elements 27 or 28, and Element 27 in combination of Element 28.

Another nonlimiting example embodiment is a composition comprising: a plurality of primary branched nitrate molecules having an empirical chemical formula of $C_nNO_3$, wherein $C_n$ is a branched aliphatic moiety, n is an integer greater than or equal to eight, and at least one carbon atom in the branched aliphatic moiety is bound to three or more carbon atoms; a plurality of branched nitrate molecules having an empirical chemical formula of $C_{n-1}NO_3$, wherein $C_{n-1}$ is a branched aliphatic moiety, n is an integer greater than or equal to eight, and at least one carbon atom in the branched aliphatic moiety is bound to three or more carbon atoms; and a plurality of primary branched nitrate molecules having an empirical chemical formula of $C_{n+1}NO_3$, wherein $C_{n+1}$ is a branched aliphatic moiety, n is an integer greater than or equal to eight, and at least one carbon atom in the branched aliphatic moiety is bound to three or more carbon atoms. Optionally, the embodiment may further include one or more of the following Elements: Element 29: the composition, characterized by a flash point of about 80° C. or greater; Element 30: the composition, having a thermal decomposition temperature as measured by thermogravimetric analysis of greater than about 132° C.; Element 31: the composition having a nitrogen content of not more than about 7.5 wt. % with respect to the total weight of the composition; Element 32: the composition wherein substantially all of the primary nitrate molecules in the composition have at least one carbon atom in the branched aliphatic moiety that is bound to three or more carbon atoms; and Element 33: the composition further comprising 2-EHN. Example combinations include, but are not limited to, Element 29 in combination with one or more of Elements 30-33; Element 30 in combination with one or more of Elements 31-33; Element 31 in combination with one or more of Elements 32 and 33; and Element 32 in combination with Element 33.

To facilitate a better understanding of the embodiments of the present invention, the following examples of preferred or representative embodiments are given. In no way should the following examples be read to limit, or to define, the scope of the invention.

EXAMPLES

Example 1: Preparation of Randomly Branched Nitrate Compositions

Each randomly branched nitrate composition is prepared from an EXXAL™ randomly branched alcohol composition containing randomly branched alcohol molecules having the empirical formula $C_nOH$, wherein n is an integer from eight to thirteen (including eight and thirteen). The EXXAL™ randomly branched alcohol composition comprises a variety of $C_n$ isomeric molecules. Table 1 provides example data related to the random distribution of methyl groups on $C_8$ randomly branched alcohol molecules making up a $C_8$ randomly branched alcohol (RBA) composition (EXXAL™ 8) from which a $C_8$ randomly branched nitrate composition may be prepared. Each value may vary by 5 wt. % or more.

TABLE 1

| First Branch Position (Carbon Atom Number) | Weight % of Total RBA Composition |
| --- | --- |
| 2 | 9% |
| 3 | 30% |
| 3 and 4 (dimethyl) | 20% |
| 4 | 27% |
| 5, 5+ | 14% |

Table 2 below characterizes the distribution of $C_n$, $C_{n\pm1}$, and $C_{n\pm2}$ molecules in example $C_n$ randomly branched alcohol compositions that may be useful for preparing a randomly branched nitrate composition as disclosed herein. Values with a hash (#) denote that the range or value listed includes $C_{n+1}$ and heavier (e.g., $C_{n+2}$, $C_{n+3}$, $C_{n+4}$) molecules.

TABLE 2

| $C_n$ of RBA Composition | Alcohol Purity (wt. %) | $C_{n-1}$ (wt. %) | $C_{n+1}$ (wt. %) | $C_{n\pm2}$ (wt. %) | $C_{4-}$ (wt. %) |
| --- | --- | --- | --- | --- | --- |
| $C_8$ | 99.0 | 0-3.5 | 2.0-9.0 | 0-1.0 | |
| $C_9$ | 99.0 | 0-6.0 | 18.0-25.0 | 0-2.5 | 0-0.5 |

TABLE 2-continued

| $C_n$ of RBA Composition | Alcohol Purity (wt. %) | $C_{n-1}$ (wt. %) | $C_{n+1}$ (wt. %) | $C_{n\pm2}$ (wt. %) | $C_{4-}$ (wt. %) |
|---|---|---|---|---|---|
| $C_{10}$ | 99.0 | 4.0-10.0 | 3.0-7.0# | n/a | 0-0.5 |
| $C_{13}$ | 98.5 | about 30 | 0-10.0# | n/a | 0-0.5 |

Table 3 below reports example randomly branched alcohol compositions that may be converted into randomly branched nitrate compositions and the predominant isomeric molecule found therein.

TABLE 3

| $C_n$ of RBA Composition | Dominant Isomers |
|---|---|
| $C_8$ | dimethyl-1-hexanol, methyl-1-heptanol |
| $C_9$ | dimethyl-1-heptanol, methyl-1-octanol |
| $C_9$* | dimethyl-1-heptanol, methyl-1-octanol |
| $C_{10}$ | trimethyl-1-heptanol, dimethyl-1-octanol |
| $C_{12}$ | Trimethyl-1-nonanol, tetramethyl-1-nonanol |
| $C_{11}$ | trimethyl-1-octanol, dimethyl-1-nonanol |

In Table 3, two randomly branched alcohol compositions having nine carbon atoms are listed ($C_9$ and $C_9$*). "$C_9$*" has a wt. % of $C_9$ randomly branched alcohol molecules than "$C_9$."

A randomly branched alcohol composition may be reacted under conditions to convert the primary alcohol moiety to a nitrate moiety, while the remaining chemical structure stays intact. One of skill in the art would know how to carry out such a reaction. For example, nitric acid in the presence of a nitric acid activating agent (e.g., sulfuric acid, acetic acid, acetic anhydride, phosphoric acid, chloroform, or the like) may be used. In another example, nitrogen pentoxide or nitrogen tetroxide may be used.

In Table 4 below, typical values for the average carbon number, the number of branches per molecule and the % of isomers with no alpha branching are shown for the alcohols that are used to make the nitrate compositions of the instant disclosure. It would be expected that the nitrate compositions of the instant disclosure made from these alcohols would have very similar branching characteristics as Table 4 because nitration will not change the structural composition of the alcohols and Table 5 below proves that conversion was pretty complete and so structural data of the nitrates will be very similar to the alcohols used to produce them.

TABLE 4

| Alcohol | Cas# | C6 | C7 | C8 | C9 | C10 | C11 | C12 | C13 | Average carbon number | Nr of branches per molecule | % of isomers with no alpha branching |
|---|---|---|---|---|---|---|---|---|---|---|---|---|
| IsoOctanol | 68526-83-0 | 0.1 | 2.8 | 91 | 5.9 | 0.5 | | | | 8 | 1.61 | 88.2 |
| IsoNonanol | 68526-84-1 | | 0.3 | 3 | 76 | 20 | 1.2 | | | 9.2 | 1.87 | 88.1 |
| IsoDecanol | 68526-85-2 | | | | 3 | 90 | 7.1 | | | 10 | 2.06 | 90.0 |
| IsoUndecanol | 68551-08-6 | | | | 0.4 | 8.9 | 84 | 6.5 | | 11 | 2.12 | 83.1 |
| Isododecanol | 68526-86-3 | | | | | 6 | 18 | 55 | 21 | 11.9 | 3.12 | 87.2 |

Example 2: Flash Point

The flash point of samples of each randomly branched nitrate (RBN) composition and a sample of 2-EHN is measured by ASTM D93-18. FIG. 1 reports each sample's measured flash point. It appears that randomly branched nitrate compositions with more carbon atoms have a higher flash point and thus may be safer to store and handle. Error bars represent method repeatability.

Example 3: Thermal Decomposition

Figure 2:
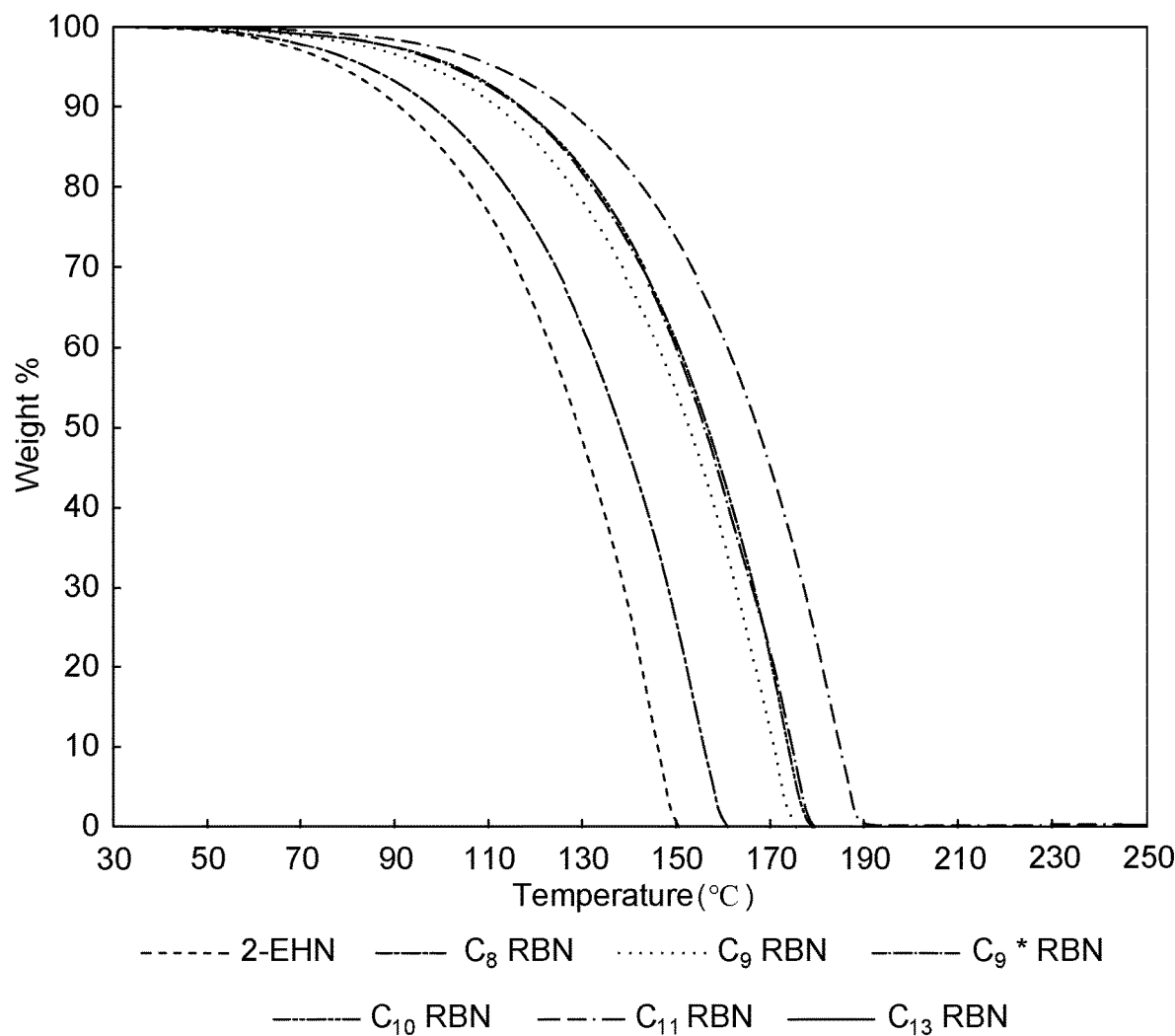
FIG. 2 provides data related to the thermal degradation of samples of various embodiments of $C_n$ randomly branched nitrate compositions disclosed herein and as described in Example 3.

Thermal decomposition of samples of each randomly branched nitrate composition and a sample of 2-EHN is evaluated by thermogravimetric analysis (TGA). TGA experiments are carried out in an inert atmosphere. Decomposition temperature is recognized as a surrogate in the industry as indicative of auto-ignition temperature. Thus, decomposition temperature is directly related to safety of storage and handling. Higher decomposition temperatures indicate that a material is more stable and thus safer to handle. FIG. 2 reports the TGA curve obtained by TGA analysis of each randomly branched nitrate composition sample and of a 2-EHN sample. It appears that 2-EHN has the lowest decomposition temperature while the decomposition temperature of each randomly branched nitrate composition seems to increase with the number of carbon atoms in randomly branched nitrate molecules therein.

Example 4: Induction Period

Figure 3A:
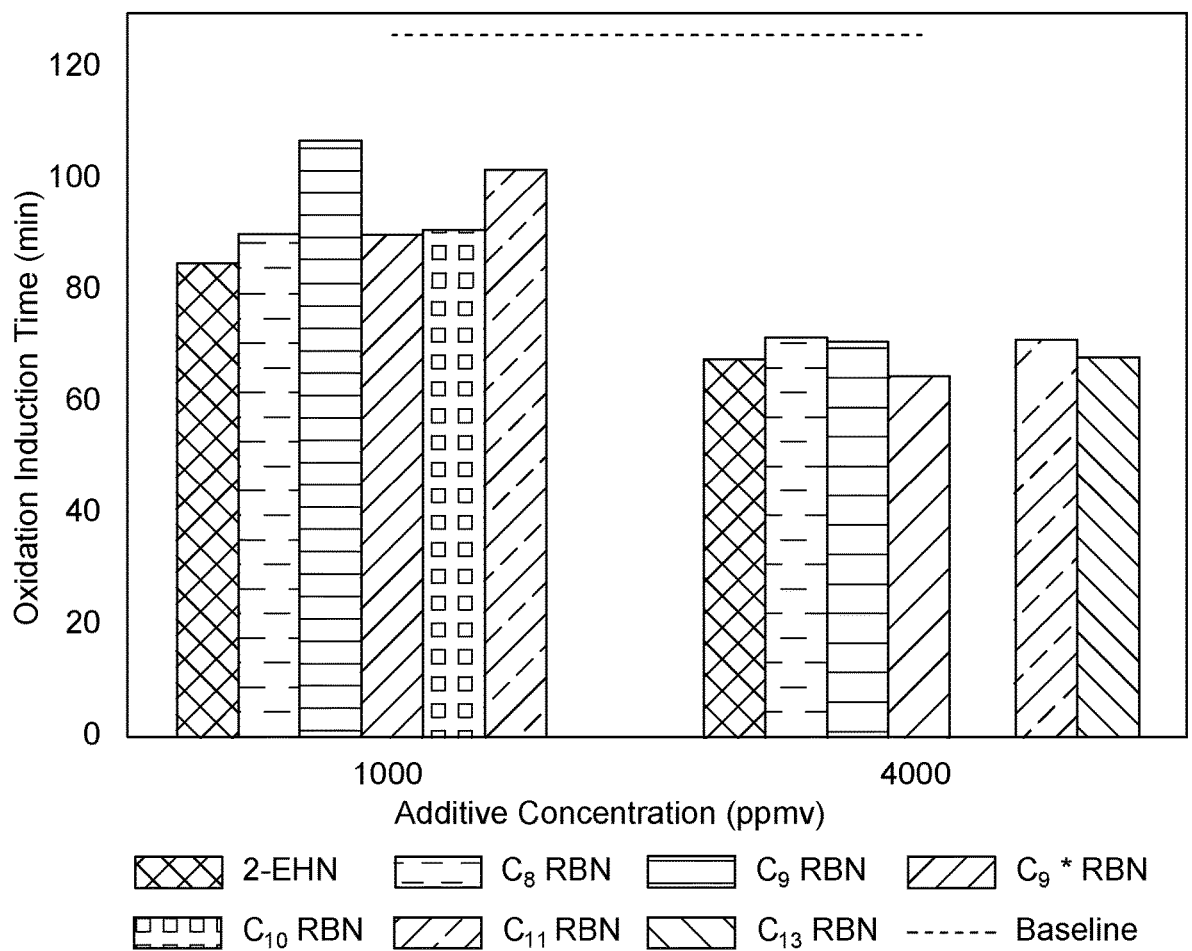
FIG. 3a provides data related to the oxidation induction time of a high aromatic diesel fuel composition (no fatty acid methyl esters (FAME)) that includes a randomly branched nitrate composition, as described in Example 4.
Figure 3B:
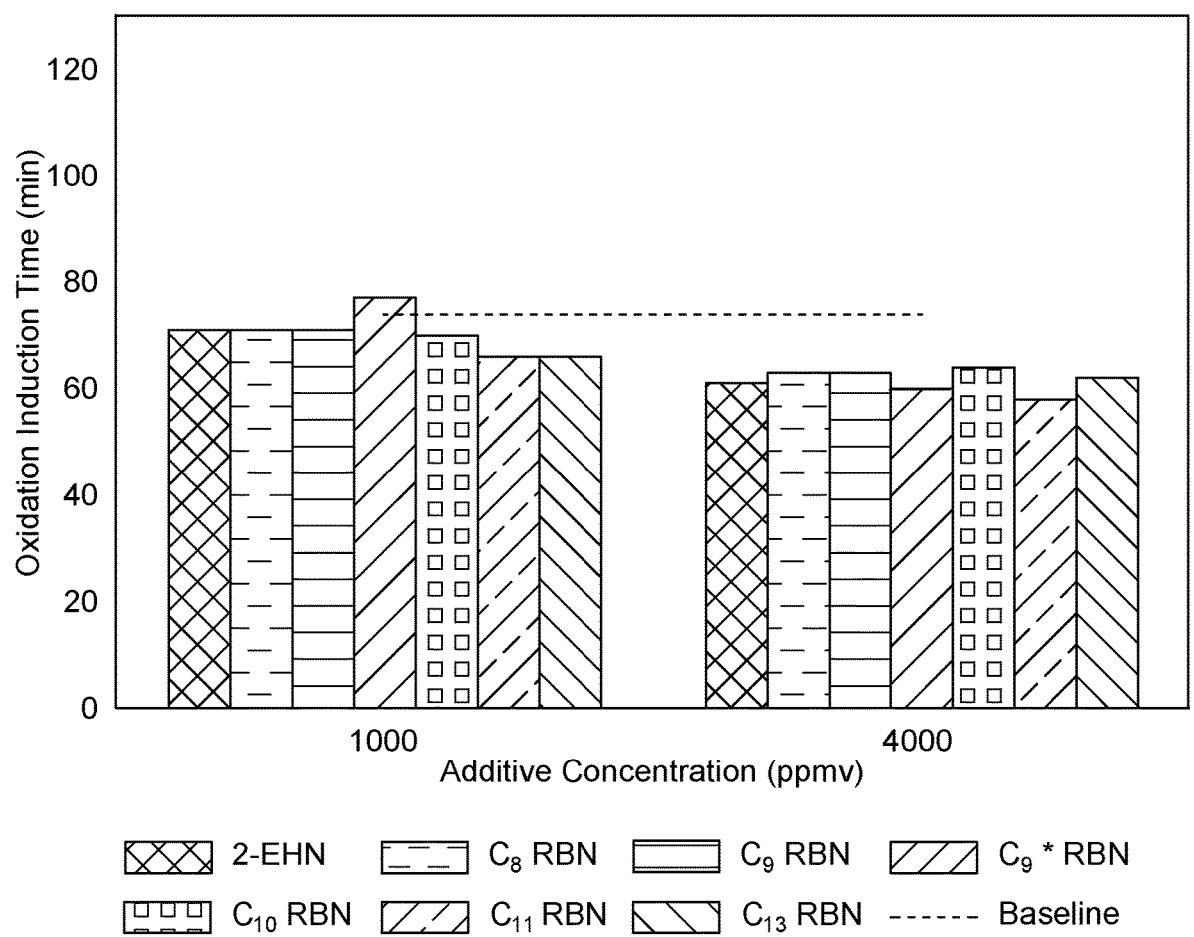
FIG. 3b provides data related to the oxidation induction time of a low aromatic diesel fuel composition (no FAME) that includes a randomly branched nitrate composition, as described in Example 4.
Figure 3C:
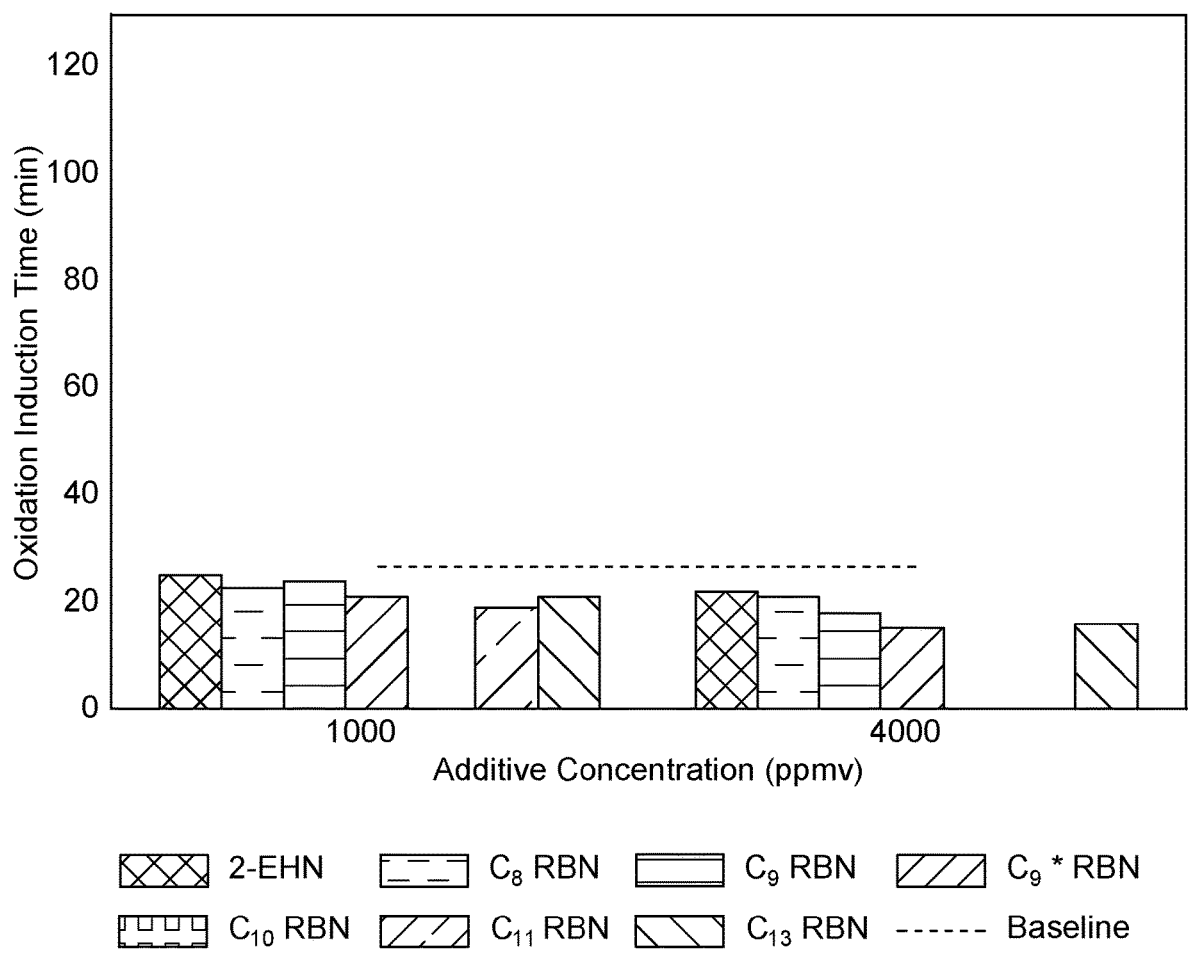
FIG. 3c provides data related to the oxidation induction time of a high aromatic diesel fuel composition (20 vol. % FAME) that includes a randomly branched nitrate composition, as described in Example 4.
Figure 3D:
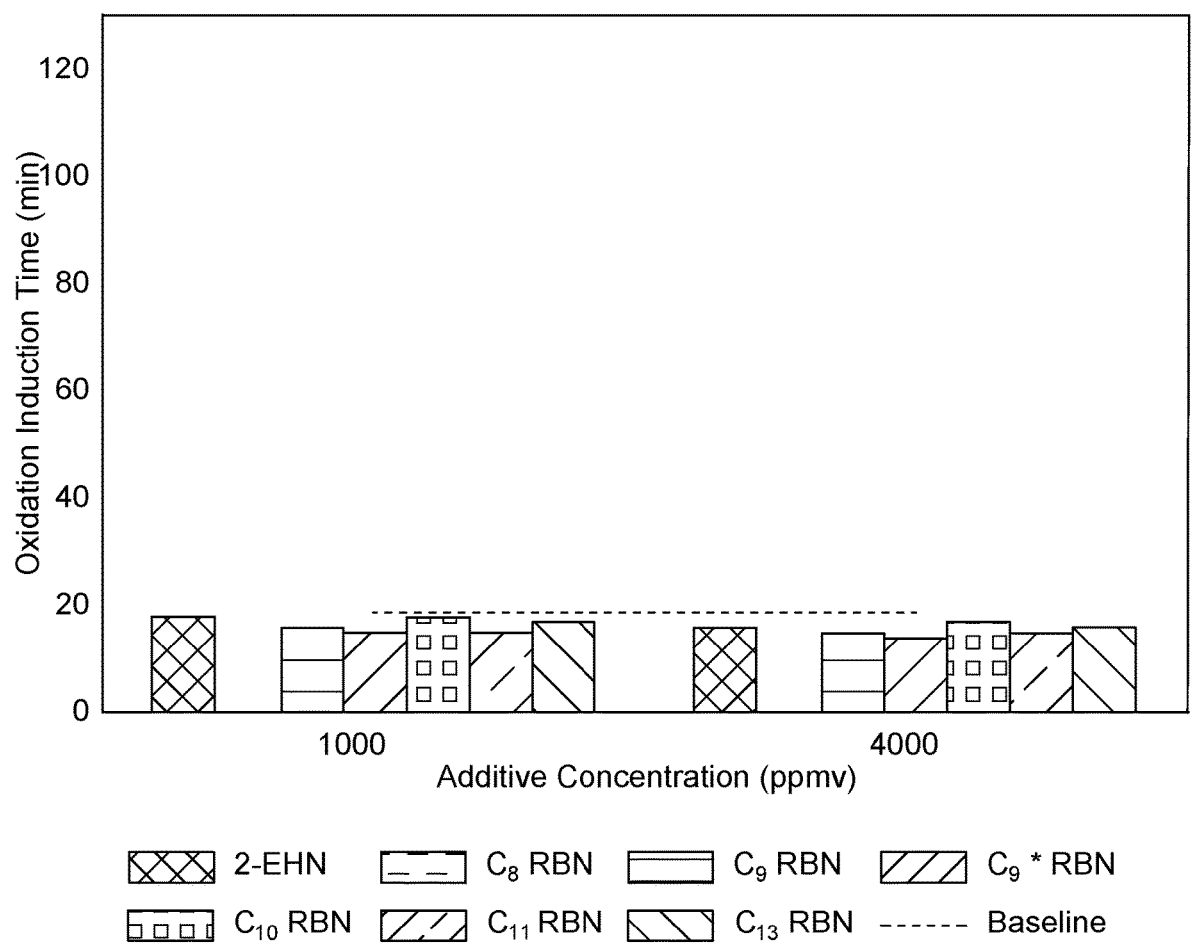
FIG. 3d provides data related to the oxidation induction time of a diesel fuel composition (20 vol. % FAME) that includes a randomly branched nitrate composition, as described in Example 4.

Induction period for samples of each randomly branched nitrate composition is measured by ASTM D7545-14 ("the PetroOXY test"). Generally, a longer the induction period corresponds to higher stability. FIGS. 3a and 3b report the induction period of each randomly branched nitrate composition as it compares to 2-EHN in a high aromatic diesel fuel composition (about 35 wt. % aromatics) and a low aromatic diesel fuel composition (about 22 wt. % aromatics), respectively. Neither contain any FAME. Error bars represent method repeatability. Data appears to illustrate that none of the randomly branched nitrate compositions significantly decrease the induction period of the fuel when compared to the induction period resulting from adding 2-EHN. The dashed line represents the base fuel without any addition of a randomly branched nitrate composition. FIGS. 3c and 3d illustrate a similar trend with a diesel fuel composition containing 20 vol. % FAME. Notably, in each of FIGS. 3a, 3b, 3c, and 3d, there appears to be no substantial reduction in induction time with any of the randomly branched nitrate compositions when compared to the induction time when using 2-EHN. On a molar basis, the use of a randomly branched nitrate composition rather than 2-EHN may provide some advantage.

Example 5: Storage Stability

Figure 4:
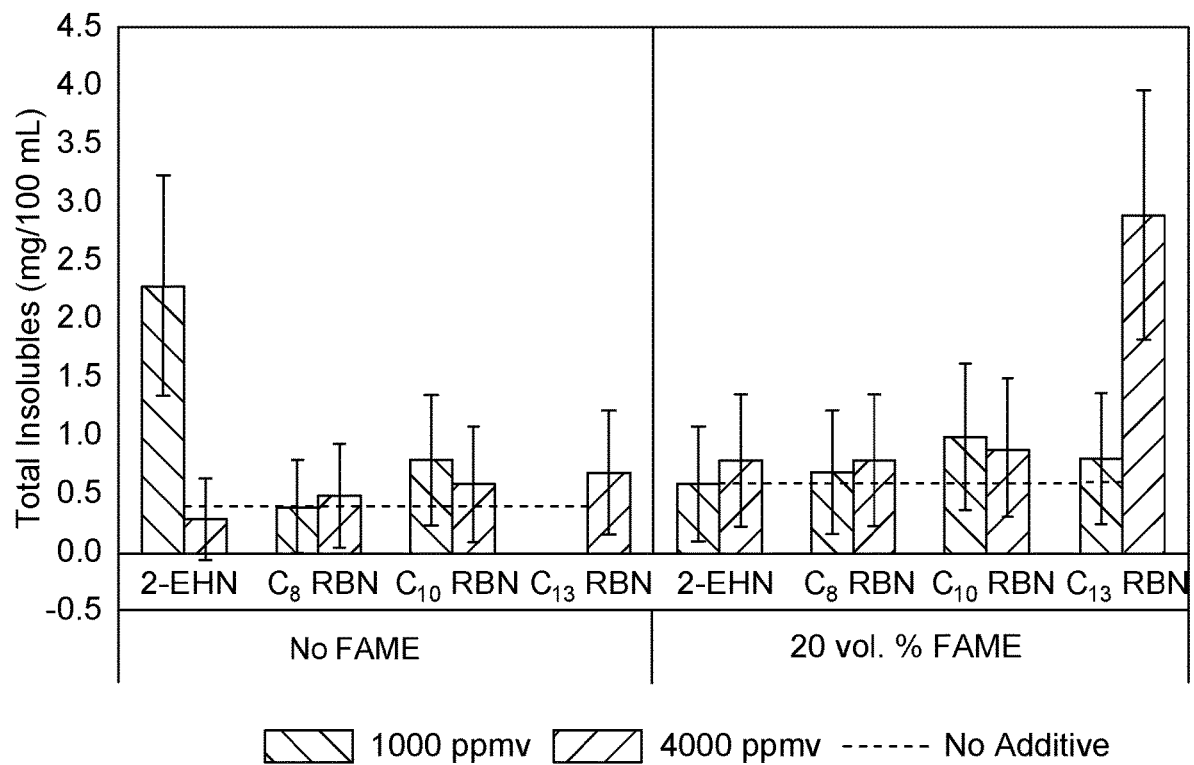
FIG. 4 provides data related to the formation of insolubles during storage of a diesel fuel composition that includes a randomly branched nitrate composition, as described in Example 5.

Over time, storage of a diesel fuel composition may result in fuel oxidation and degradation, forming sediment. The effect of each randomly branched nitrate composition on sediment formation in the diesel fuel composition to which it is added is measured by ASTM D4625-16e1. Samples are stored for six weeks at 43° C. (which, in industry, is considered indicative of storage at ambient temperature for 6 months), after which total insolubles in each stored sample are measured. FIG. 4 reports the results of these studies. Error bars are method repeatability. It appears that the diesel fuel compositions containing a randomly branched nitrate composition show similar or improved storage stability after 6 weeks compared to a diesel fuel composition containing 2-EHN. In any case, randomly branched nitrate compositions do not reduce the storage stability of diesel fuel compositions as compared to a diesel fuel composition with 2-EHN.

Example 6: Nitrogen Content

The nitrogen content in samples of various $C_n$ randomly branched nitrate compositions prepared from $C_n$ randomly branched alcohol compositions is measured by combustion and chemiluminescence. Table 5 below provides measured nitrogen and calculated nitrogen for each $C_n$ randomly branched nitrate composition. 2-EHN and a $C_8$ randomly branched nitrate composition have the same nitrogen content. Additionally, the efficiency of conversion of the randomly branched alcohol (RBA) compositions described in Tables 2 and 3 to $C_n$ randomly branched nitrate (RBN) compositions is calculated.

TABLE 5

| $C_n$ in RBN Composition | Measured N Content (wt. %) | Estimated Molecular Weight | Calculated N Content (wt. %) | RBA to RBN conversion |
| --- | --- | --- | --- | --- |
| $C_8$ | 6.77 | 176.4 | 7.94 | 85.3% |
| $C_9$ | 6.57 | 191.8 | 7.3 | 90.0% |
| $C_9$* | 6.85 | 189 | 7.41 | 92.4% |
| $C_{10}$ | 6.54 | 204.4 | 6.85 | 95.5% |
| $C_{11}$ | 6.08 | 215.6 | 6.49 | 93.7% |
| $C_{13}$ | 5.52 | 239.4 | 5.85 | 94.3% |

Example 7: Diesel Cetane Enhancement

Figure 5A:
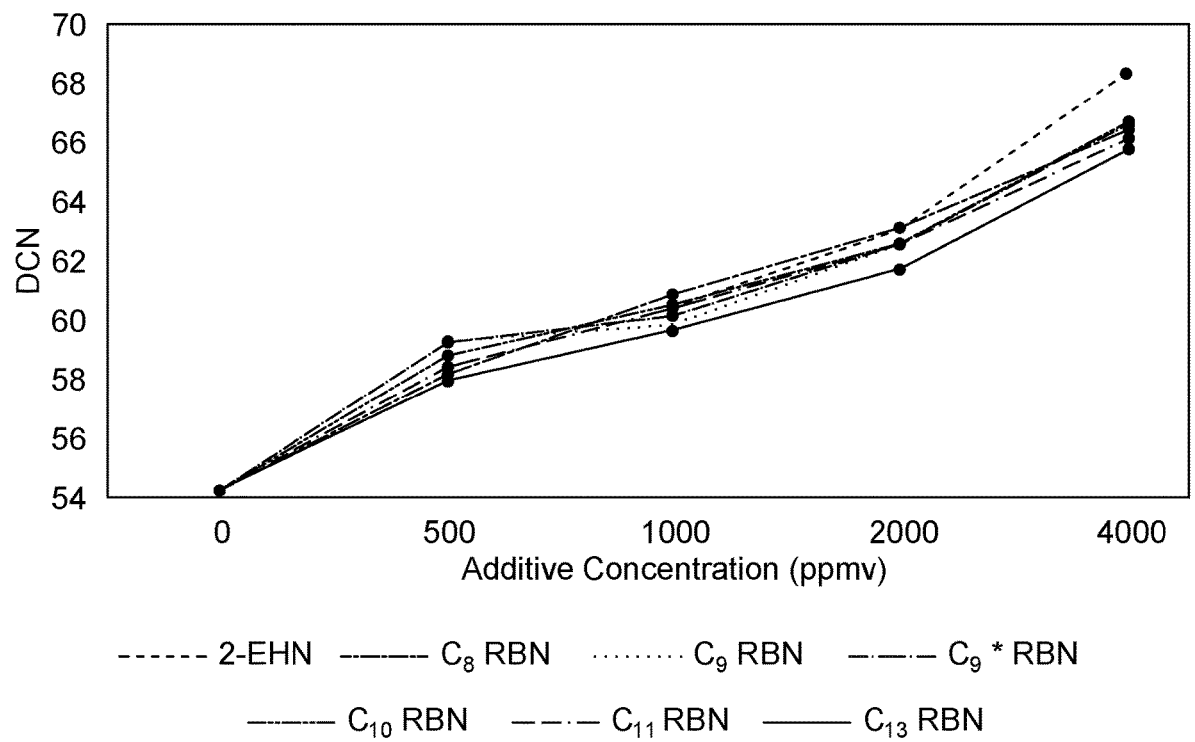
FIG. 5a provides data related to the achieved derived cetane number (DCN) of a diesel fuel composition (no FAME) that includes a randomly branched nitrate composition, as described in Example 7.
Figure 5B:
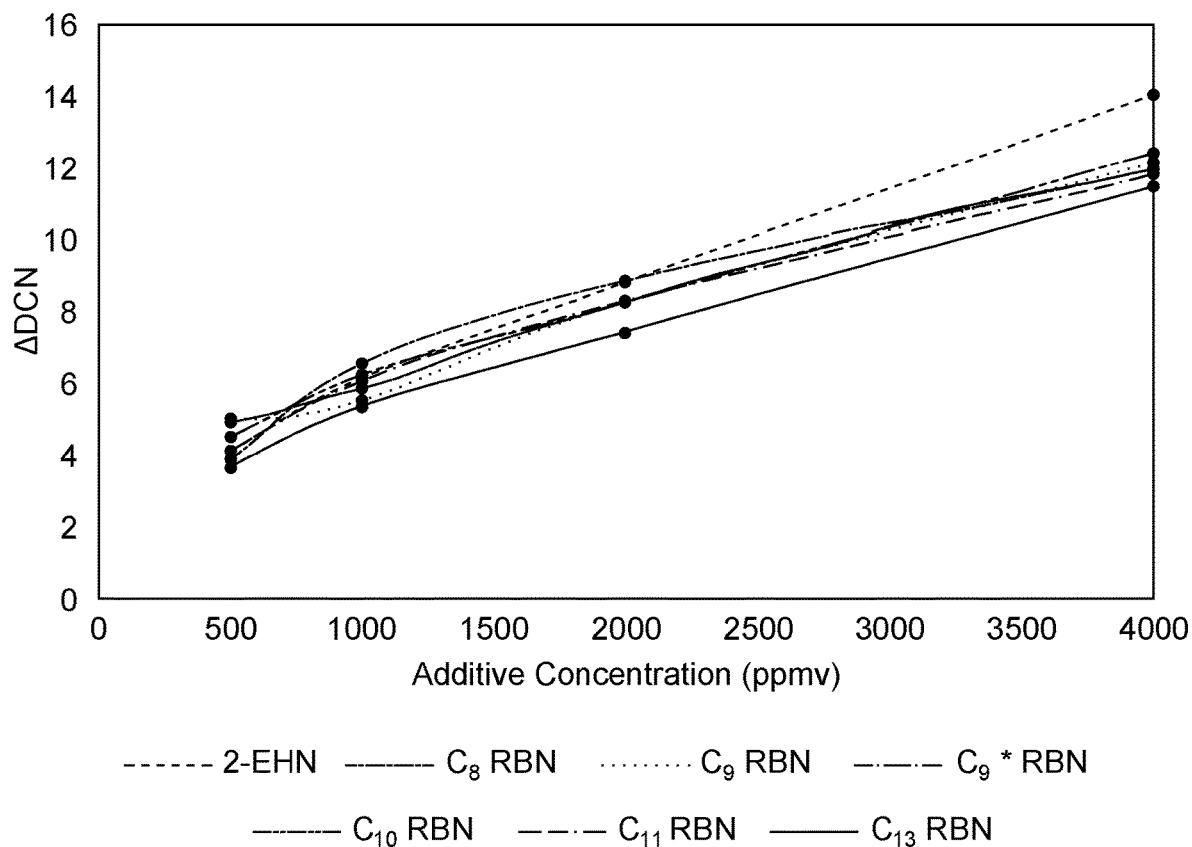
FIG. 5b provides data related to the effect of adding a randomly branched nitrate composition to a base diesel fuel composition (no FAME) on DCN, as described in Example 7.

2-EHN and various $C_n$ randomly branched nitrate compositions varying from about 0 ppmv to about 4000 ppmv are added to a base diesel fuel composition (no FAME) that meets the EN590 Standard in Europe. Samples of each are analyzed for cetane number using a Herzog CID510 analyzer, according to ASTM D7668-17, to determine DCN of each sample. FIG. 5a illustrates the achieved DCN as a function of additive concentration for diesel fuel compositions containing either 2-EHN or a randomly branched nitrate composition. FIG. 5b shows the change in DCN from the DCN of the base diesel fuel composition.

A similar response is observed for each of the randomly branched nitrate compositions. The only slight deviation appears to be at the 4000 ppmv concentrations, however, as per the ASTM D7668-17 test method, test-to-test repeatability for cetane measurement is approximately ±1 DCN. Thus, all data points up to about 2000 ppmv are approximately equal, while there appears to be a slightly lower response at the 4000 ppmv level. In practice, a cetane improver is added to most diesel fuels at concentrations closer to about 1000 ppmv, so the reduction in DCN at higher concentrations may not be critical.

Figure 6A:
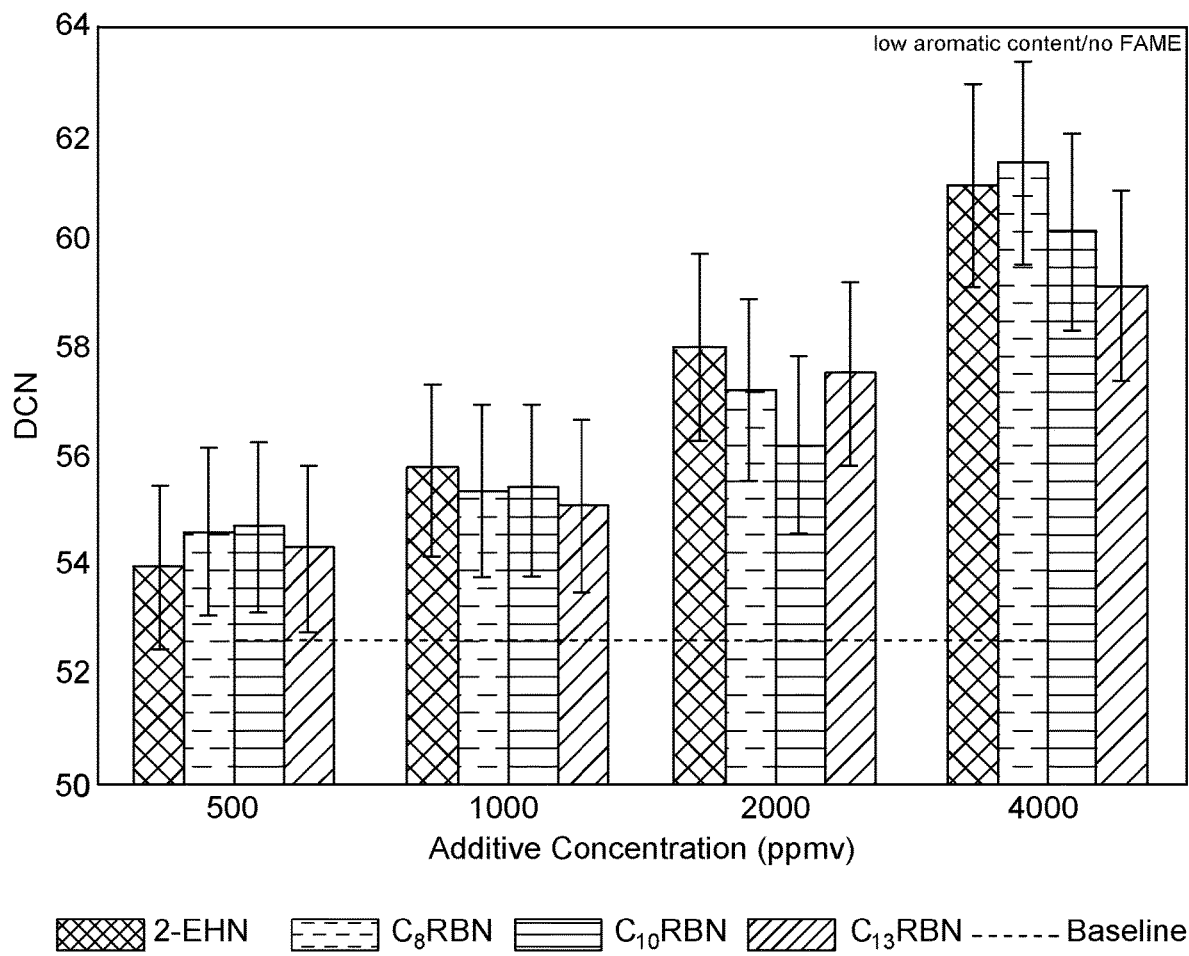
FIG. 6a provides data related to the achieved derived cetane number (DCN) of a low aromatic diesel fuel composition (no FAME) that includes a randomly branched nitrate composition, as described in Example 7.
Figure 6B:
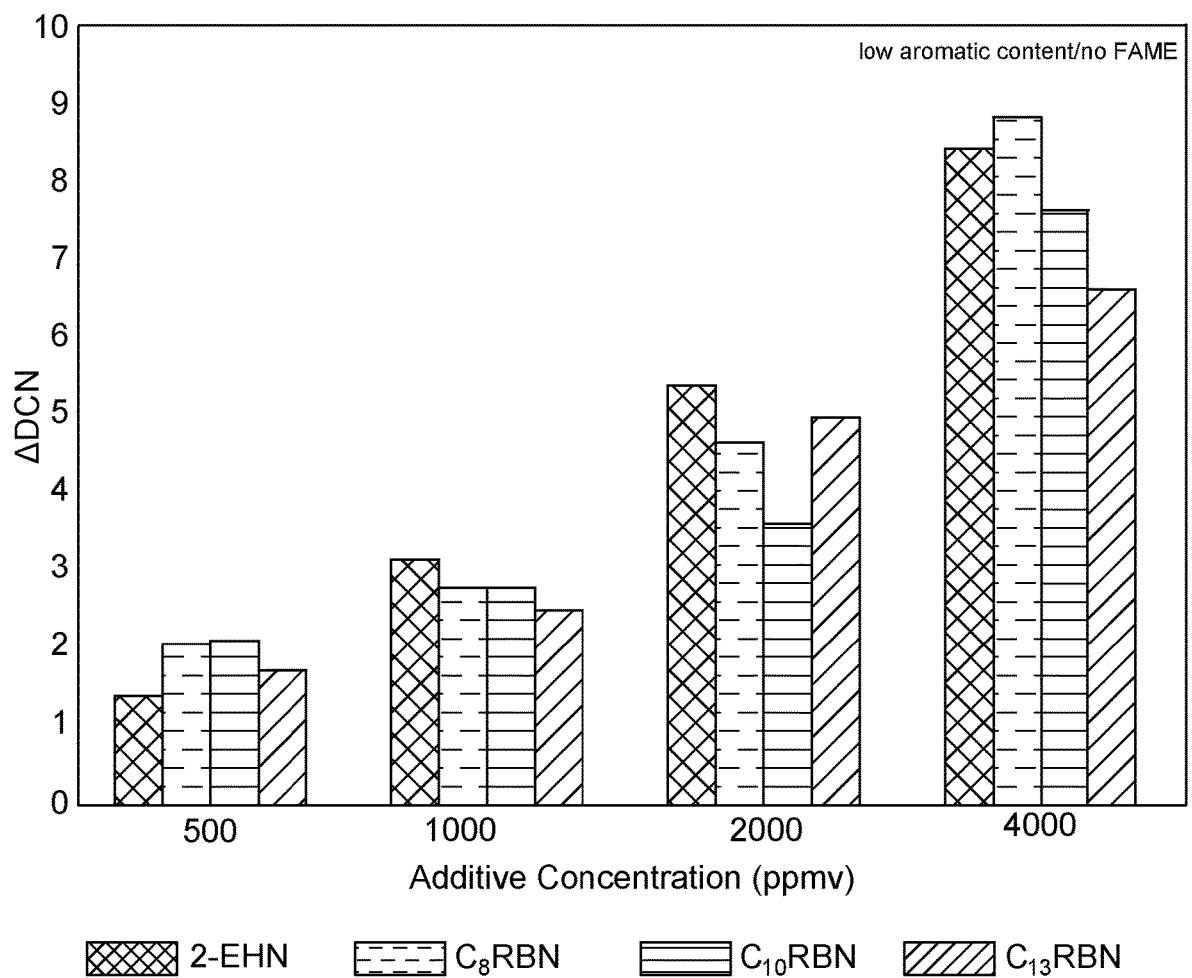
FIG. 6b provides data related to the achieved derived cetane number (DCN) of a low aromatic diesel fuel composition (no FAME) that includes a randomly branched nitrate composition, as described in Example 7.
Figure 6C:
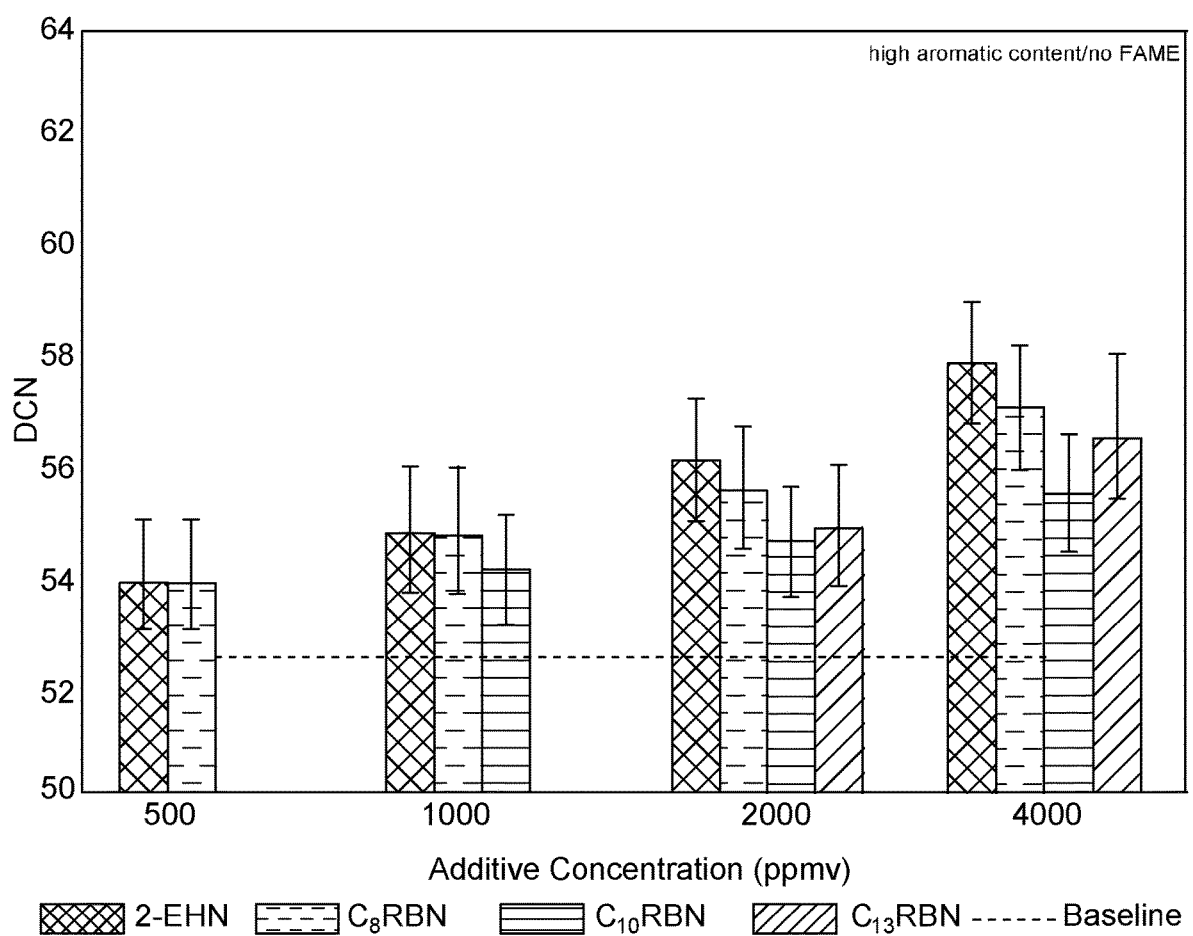
FIG. 6c provides data related to the achieved derived cetane number (DCN) of a high aromatic diesel fuel composition (no FAME) that includes a randomly branched nitrate composition, as described in Example 7.
Figure 6D:
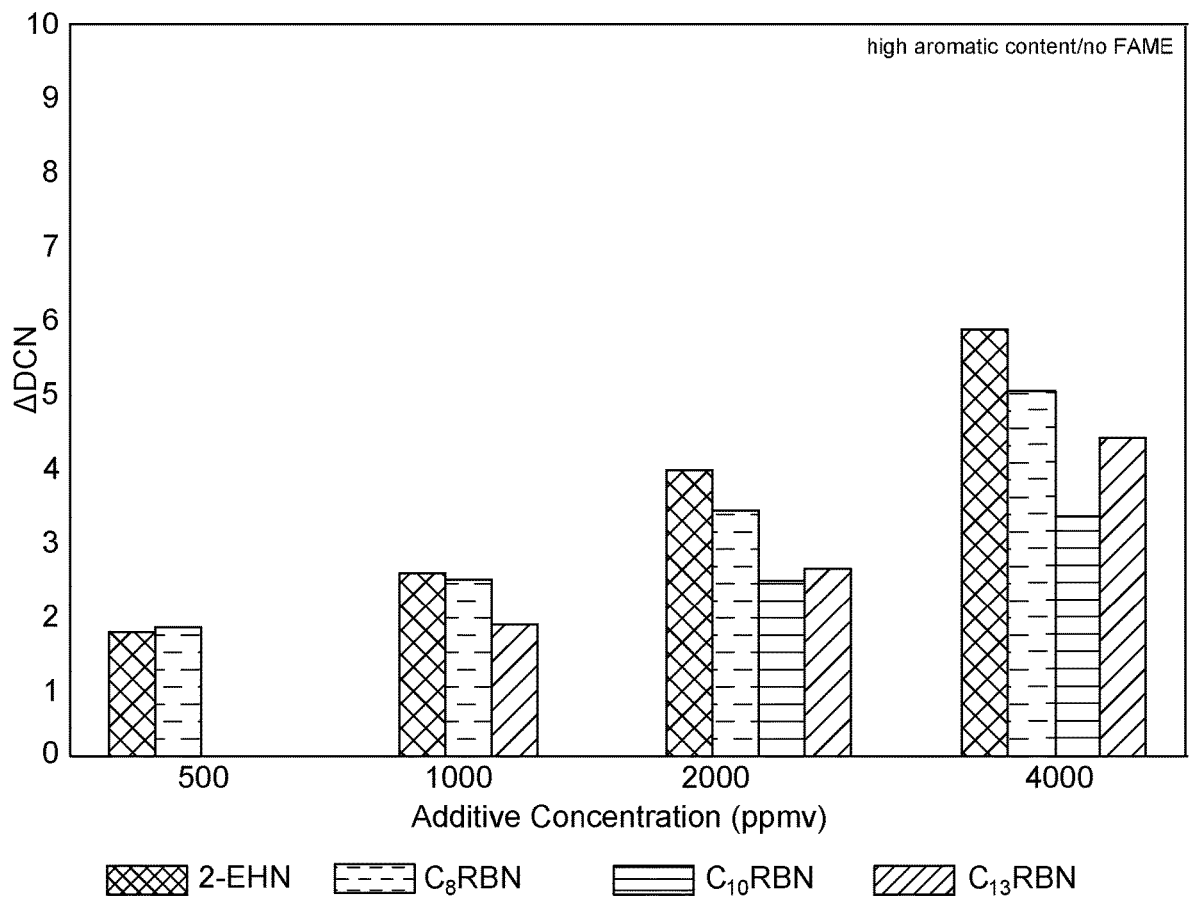
FIG. 6d provides data related to the achieved derived cetane number (DCN) of a high aromatic diesel fuel composition (no FAME) that includes a randomly branched nitrate composition, as described in Example 7.
Figure 7A:
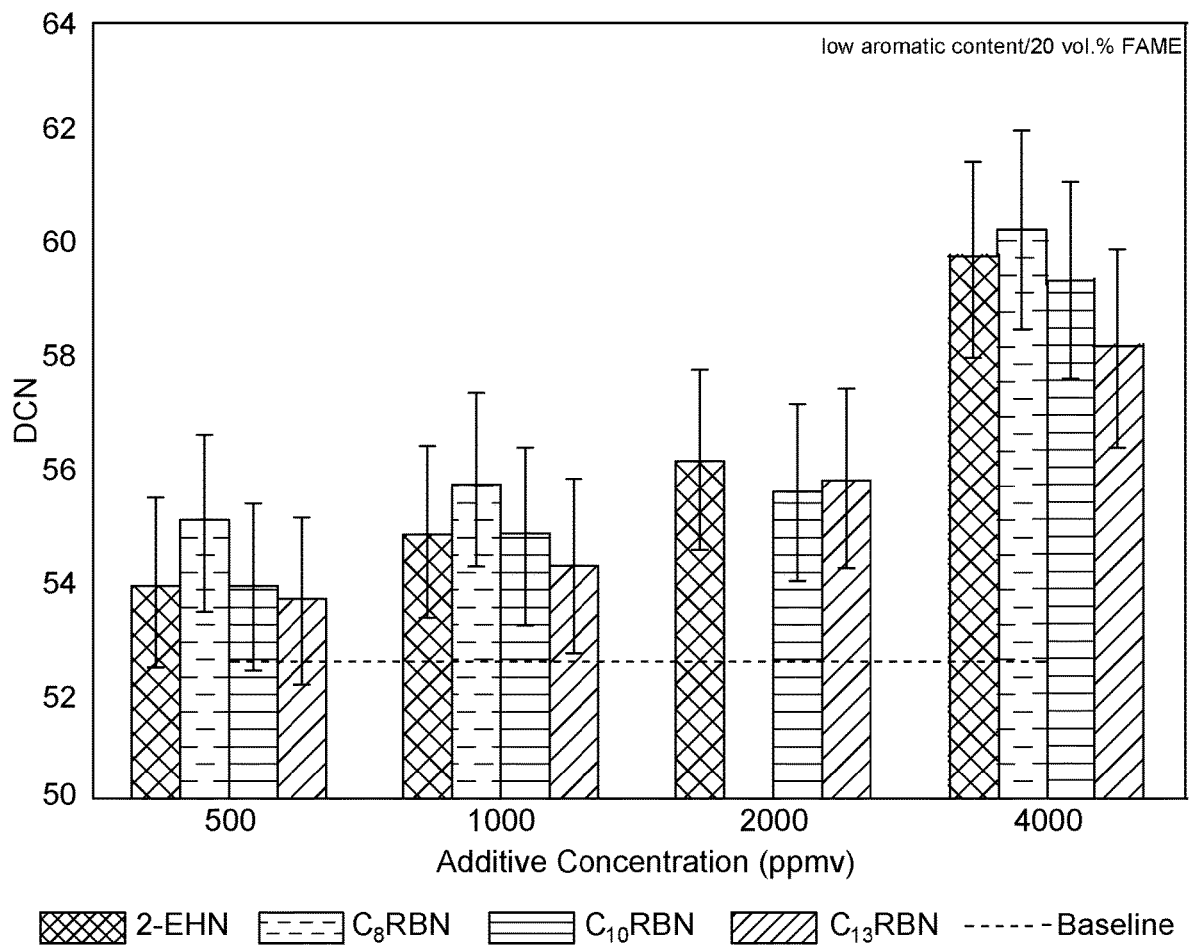
FIG. 7a provides data related to the achieved derived cetane number (DCN) of a low aromatic diesel fuel composition (20 vol. % FAME) that includes a randomly branched nitrate composition, as described in Example 7.
Figure 7B:
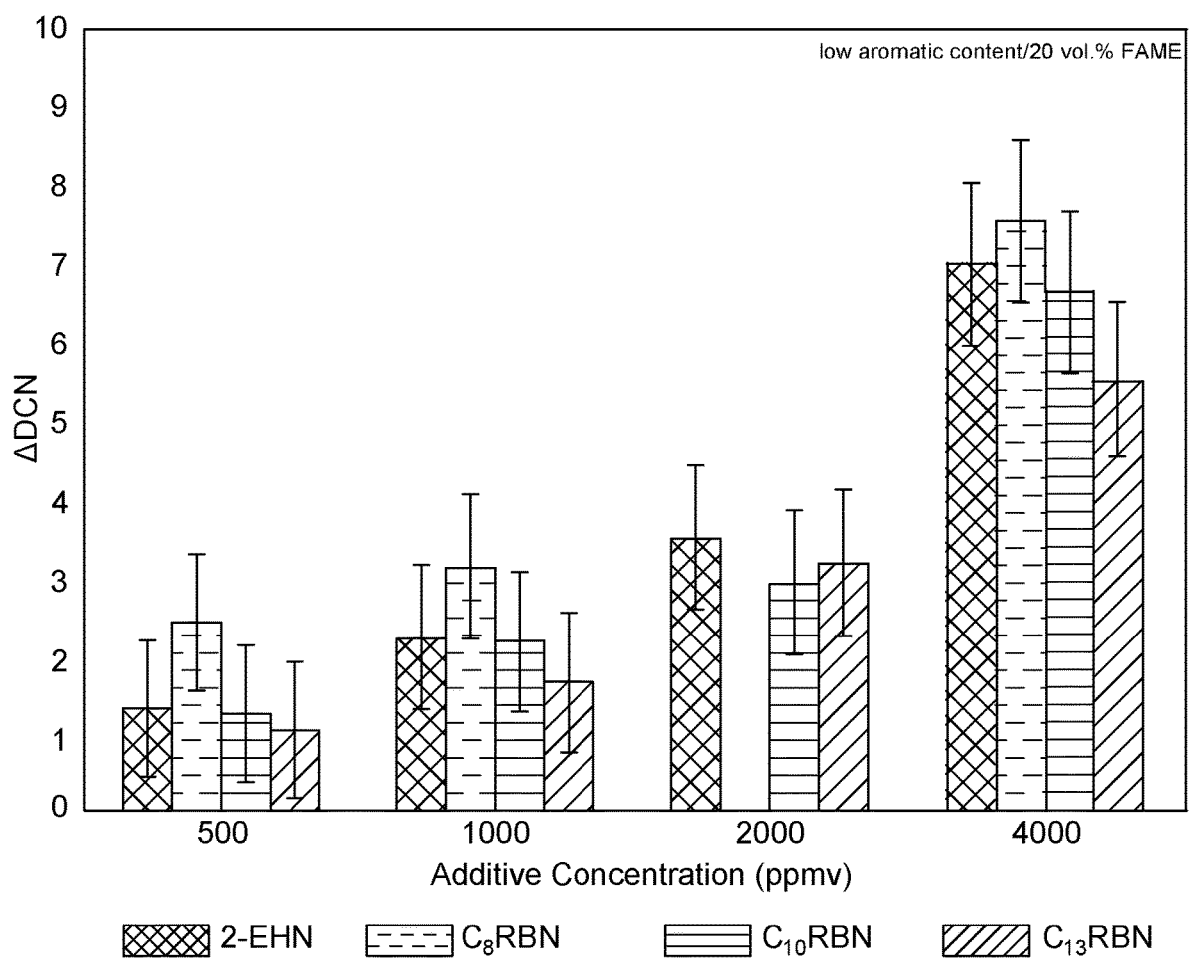
FIG. 7b provides data related to the achieved derived cetane number (DCN) of a low aromatic diesel fuel composition (20 vol. % FAME) that includes a randomly branched nitrate composition, as described in Example 7.
Figure 7C:
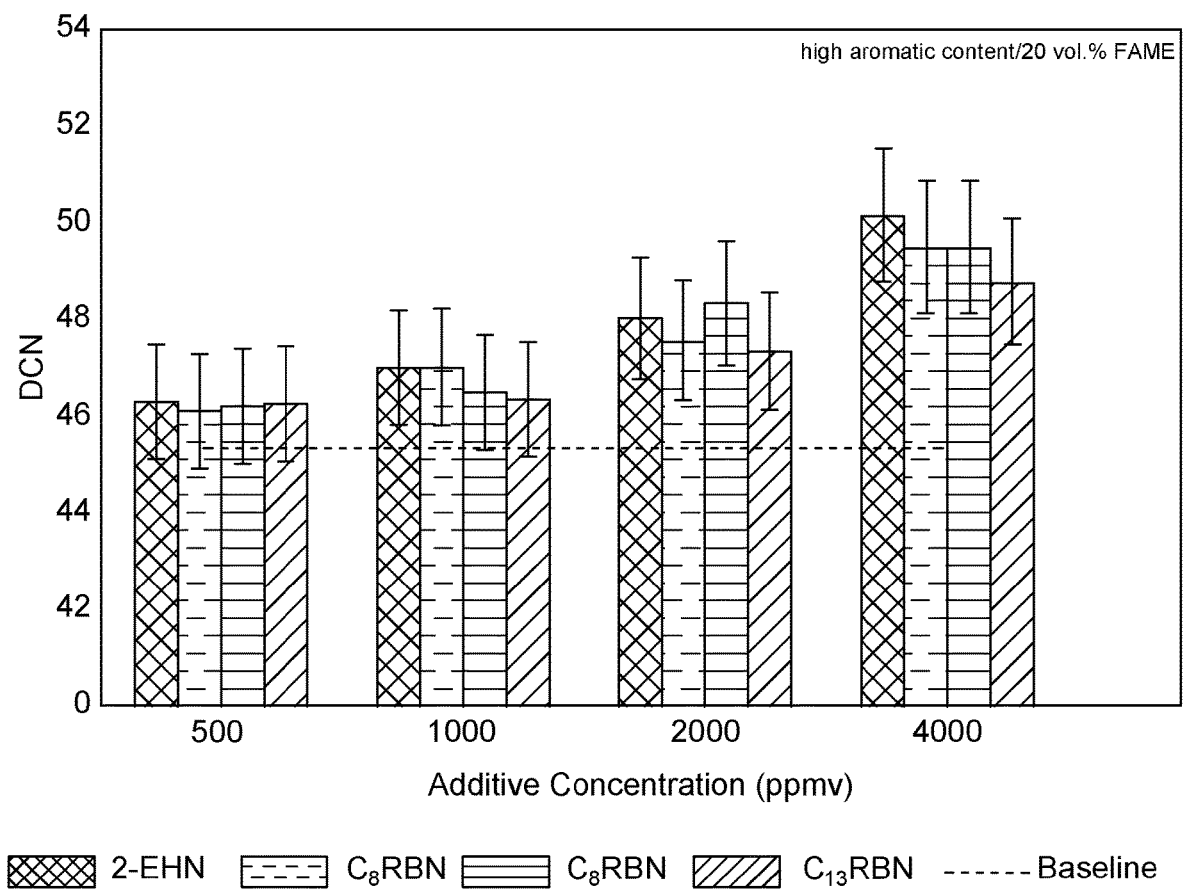
FIG. 7c provides data related to the achieved derived cetane number (DCN) of a high aromatic diesel fuel composition (20 vol. % FAME) that includes a randomly branched nitrate composition, as described in Example 7.
Figure 7D:
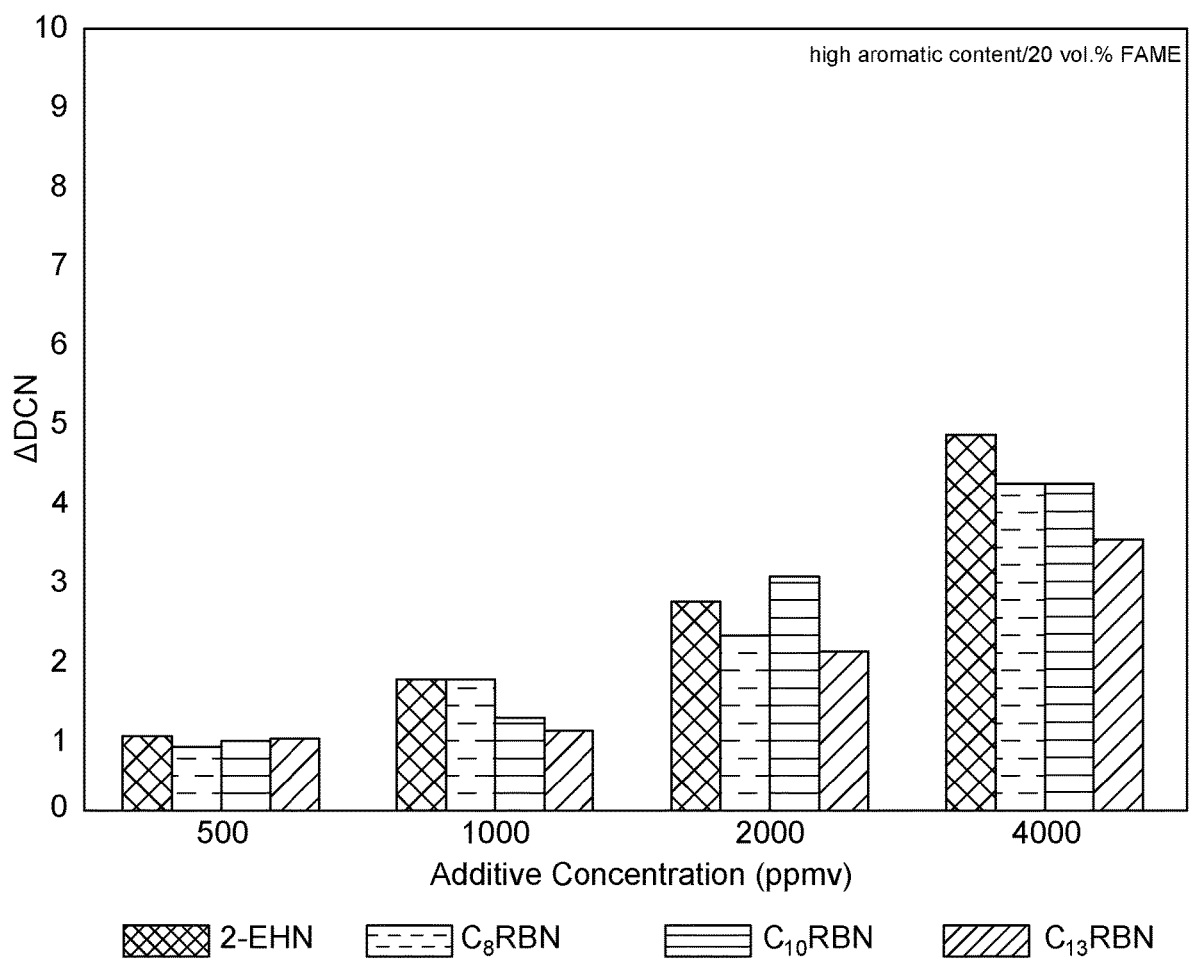
FIG. 7d provides data related to the achieved derived cetane number (DCN) of a high aromatic diesel fuel composition (20 vol. % FAME) that includes a randomly branched nitrate composition, as described in Example 7.

Further experiments were performed to investigate performance of the randomly branched nitrate compositions in base diesel compositions with varying aromatic content. FIGS. 6a and 6b illustrate the effect of using various concentrations of various randomly branched nitrate compositions on the DCN of a low aromatic (about 22 wt. % aromatics) base diesel composition (no FAME). FIGS. 6c and 6d illustrate the effect of using various concentrations of various randomly branched nitrate compositions on the DCN of a high aromatic (about 35 wt. % aromatics) base diesel composition (no FAME). FIGS. 7a and 7b illustrate the effect of using various concentrations of various randomly branched nitrate compositions on the DCN of a low aromatic (about 22 wt. % aromatics) base diesel composition (20 vol. % FAME). FIGS. 7c and 7d illustrate the effect of using various concentrations of various randomly branched nitrate compositions on the DCN of a high aromatic (about 35 vol. % aromatics) base diesel composition (20 vol. % FAME). It appears that, in many of the experiments, the randomly branched nitrate composition performs around the same or better than in both low and high aromatic base diesel compositions with and without a biodiesel (FAME) component. Thus, the randomly branched nitrate compositions disclosed herein may provide an alternative to 2-EHN that is similarly effective while, at the same time, reducing storage and safety concerns as well as $NO_x$ emissions.

Example 8: Gasoline Octane Reduction

Figure 8A:
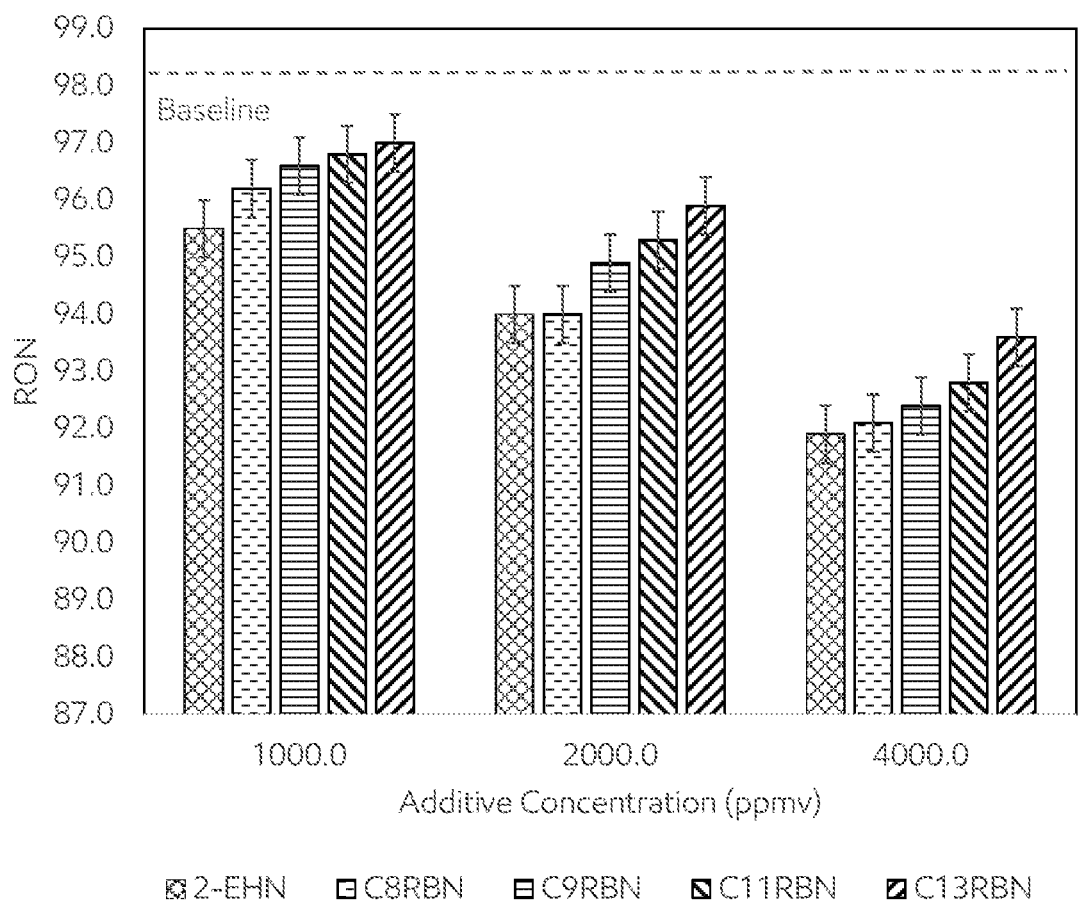
FIG. 8a provides data related to the achieved research octane number (RON) of a gasoline fuel composition that includes a randomly branched nitrate composition as described in Example 8.
Figure 8B:
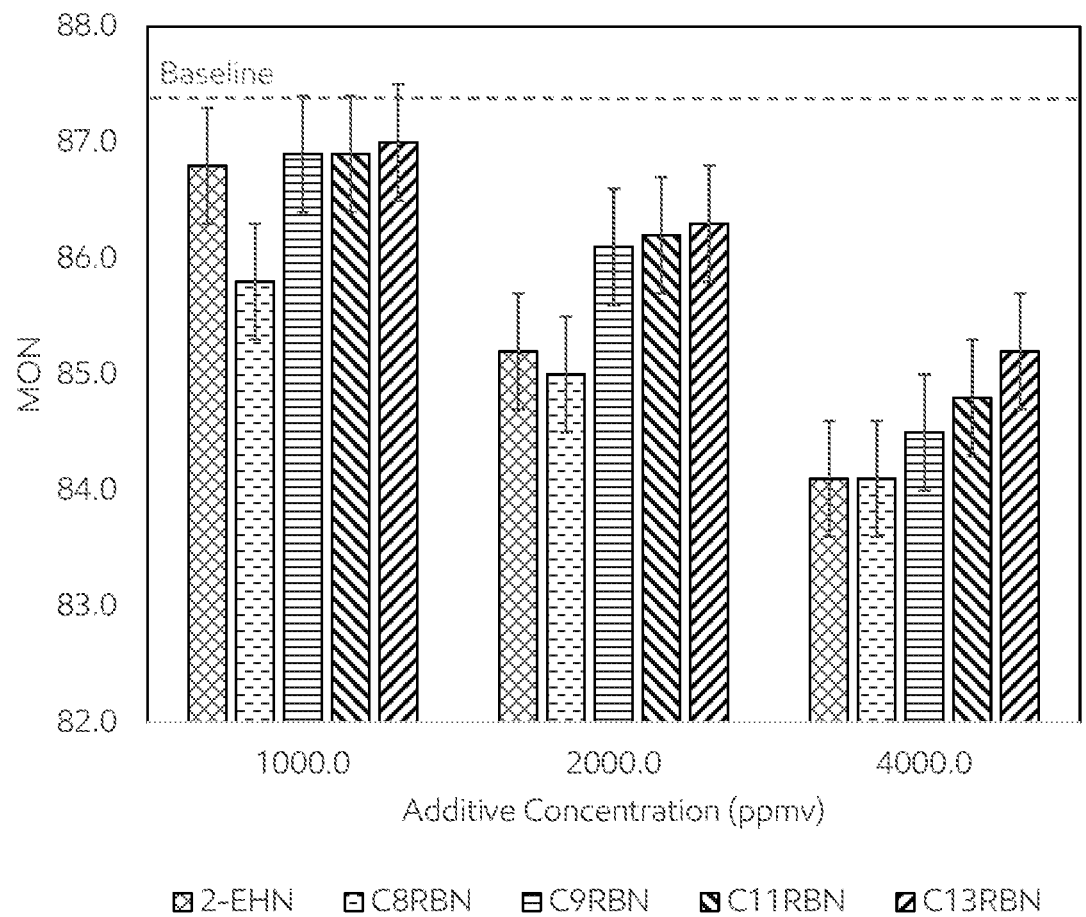
FIG. 8b provides data related to the achieved motored octane number (MON) of a gasoline fuel composition that includes a randomly branched nitrate composition as described in Example 8.
Figure 8C:
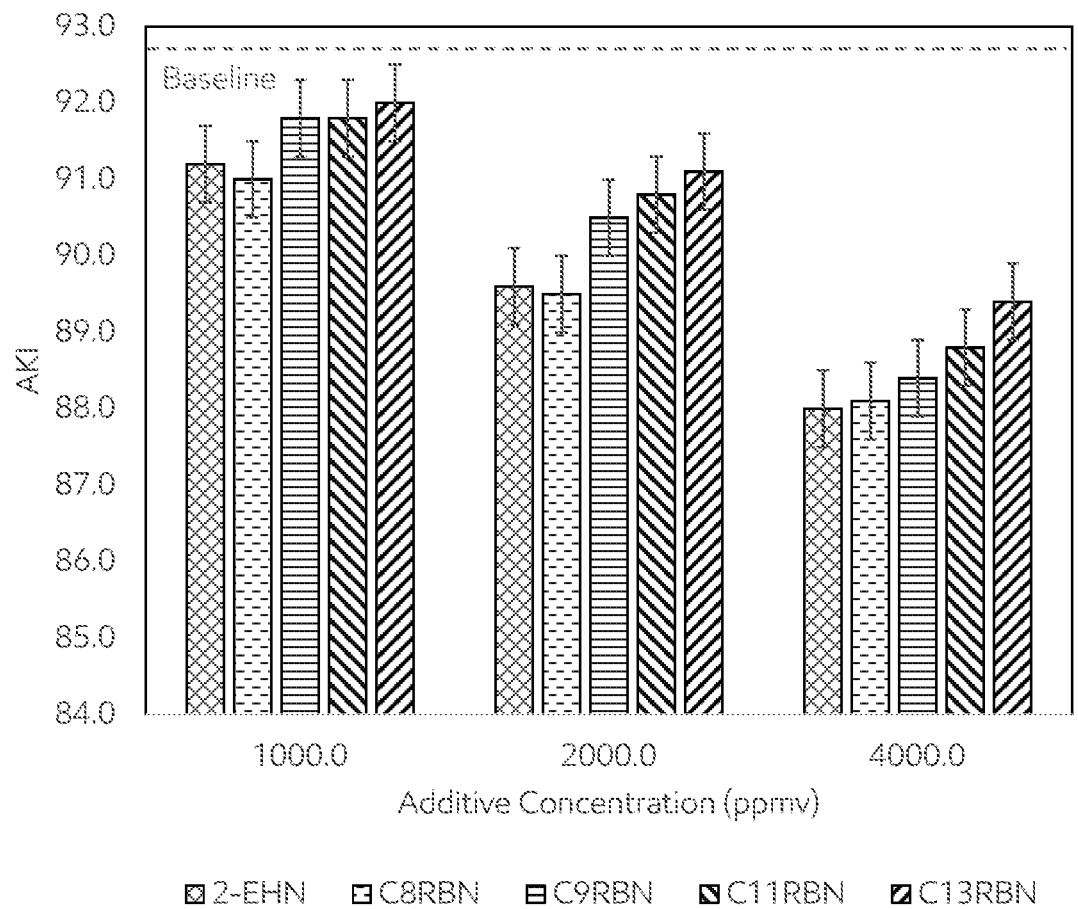
FIG. 8c provides data related to the achieved anti-knock index (AKI) of a gasoline fuel composition that includes a randomly branched nitrate composition as described in Example 8.

2-EHN and various $C_n$ randomly branched nitrate compositions varying from about 0 ppmv to about 4000 ppmv were added to a base gasoline fuel composition. Samples of each were analyzed for octane numbers using a cooperative fuel research (CFR) engine, according to ASTM D2669 and D2770 respectively, to determine RON and MON of each sample. FIG. 8 illustrates the achieved RON, MON and AKI as a function of additive concentration for gasoline fuel compositions containing either 2-EHN or a randomly branched nitrate composition. FIG. 8a illustrates a similar response to RON reductions observed for each of the randomly branched nitrate compositions with 1000 ppmv concentration. The only slight deviation appears to be at the 1000 ppmv concentrations, however, test-to-test repeatability for octane measurements is approximately ±0.5. The deviation appears to increase as additive concentration increases up to 4000 ppmv concentration. FIG. 8b illustrates a strong effect of Exxal 8 nitrate with 1000 and 2000 ppmv concentrations on MON reductions as compared to other Exxal nitrates and 2-EHN with the same concentrations, while other Exxal nitrates shows a similar response to the MON reduction. Exxal nitrates with 4000 ppmv concentrations display a common response to RON and MON reductions in respect to carbon numbers of Exxal nitrates, where higher carbon numbers of Exxal nitrates offer smaller reactivity changes represented in the octane ratings. Consequently, the same results appear in AKI of fuels with each of the randomly branched nitrate compositions, as shown in FIG. 8c. For vehicle using LTC concepts, which selectively introduce the randomly branched nitrates to the combustion process from the onboard system, these randomly branched nitrates may require higher dosage than 2-EHN because the RON and MON reduction is smaller than 2-EHN. The higher additive dosing is not a concern because it only requires in narrow engine operating conditions. Thus, the randomly branched nitrate compositions disclosed herein may provide an alternative to 2-EHN that is similarly effective while, at the same time, reducing storage and safety concerns, especially when considered storing the additives on-board, as well as NOx emissions.

PCT Clauses:

1. An additized fuel composition comprising: a base fuel composition, and a randomly branched nitrate composition comprising a plurality of primary nitrate molecules, each molecule therein having an empirical chemical formula of CnNO3, wherein Cn is a branched aliphatic moiety which may be the same or different for each molecule, n is an integer selected from the group consisting of 8, 9, 10, 11 and 12, at least one carbon atom in the branched aliphatic moiety being bound to three or more carbon atoms, a branching index ranging from 1.8 to 2.2, and greater than 80% of the branches in the aliphatic moiety being in other than the alpha position; and wherein the additized fuel composition is a diesel fuel composition or a gasoline fuel composition.

2. The fuel composition as in clause 1, wherein the base fuel composition comprises a biofuel.

3. The fuel composition as in any one of clauses 1-2, wherein the base fuel composition comprises a fatty acid methyl ester, a fatty acid ethyl ester, hydrotreated vegetable oil, or a blend thereof.

4. The fuel composition as in any one of clauses 1-3, wherein the concentration of $C_nNO_3$ molecules in the randomly branched nitrate composition is at least about 60 wt. %, preferably wherein the concentration of $C_nNO_3$ molecules in the randomly branched nitrate composition is at least about 60 wt. % and less than about 98 wt. %.

5. The fuel composition as in as in any one of clauses 1-4, wherein one of the carbon atoms bound to the at least one carbon atom in the branched aliphatic moiety is part of a methyl group.

6. The fuel composition as in any one of clauses 1-5, wherein the randomly branched nitrate composition further comprises: a primary nitrate molecule having an empirical chemical formula of $C_{n-1}NO_3$, wherein $C_{n-1}$ is a branched aliphatic moiety, n is an integer greater than or equal to eight, and at least one carbon atom in the branched aliphatic moiety is bound to three or more carbon atoms; and a primary nitrate molecule having an empirical chemical formula of $C_{n+1}NO_3$, wherein $C_{n+1}$ is a branched aliphatic moiety, n is an integer greater than or equal to eight, and at least one carbon atom in the branched aliphatic moiety is bound to three or more carbon atoms.

7. The fuel composition as in any one of clauses 1-6, wherein the randomly branched nitrate composition is present at a concentration of about 500 ppmv to about 4000 ppmv, preferably wherein the randomly branched nitrate composition is present at a concentration of about 500 ppmv to about 2000 ppmv.

8. The fuel composition as in any one of clauses 1-7, wherein when said fuel composition is combusted in the presence of oxygen, a lower mass of nitrogen oxide and nitrogen dioxide is produced than the mass of nitrogen oxide and nitrogen dioxide produced from the combustion of a fuel composition comprising the base fuel composition and a concentration of 2-ethylhexyl nitrate equal to the concentration of the randomly branched nitrate composition in the fuel composition.

9. The fuel composition as in any one of clauses 1-8, wherein the additized fuel composition is a diesel fuel composition and wherein after storage of the diesel fuel composition comprising about 1000 ppmv of the randomly branched nitrate composition for about six weeks at about 43° C., the diesel fuel composition comprises less than about 1.0 mg/100 mL of insoluble material as measured according to ASTM D4625-16e1.

10. The fuel composition as in any one of clauses 1-8, wherein the additized fuel composition is a gasoline fuel composition further comprising at least one oxygenate selected from the group consisting of di-isopropyl ether, C5 ether, C6 ether, ethanol, methanol, propanol, 2-propanol, butanol, 2-butanol, iso-butanol, tert-butanol, and mixtures thereof.

11. A method for making an additized fuel composition comprising: providing a base fuel composition; and adding a randomly branched nitrate composition to the base fuel composition to form an additized fuel composition, the randomly branched nitrate composition comprising a plurality of primary nitrate molecules, each primary nitrate molecule having an empirical chemical formula of $C_nNO_3$, wherein $C_n$ is a branched aliphatic moiety which may be the same or different for each molecule, n is an integer selected from the group consisting of 8, 9, 10, 11 and 12, at least one carbon atom in the branched aliphatic moiety being bound to three or more carbon atoms, a branching index ranging from 1.8 to 2.2, and greater than 80% of the branches in the aliphatic moiety being in other than the alpha position; and wherein the additized fuel composition is a diesel fuel composition or a gasoline fuel composition.

12. The method as in clause 11, wherein the fuel composition has a higher derived cetane number than the base fuel composition, preferably wherein the derived cetane number of the fuel composition is greater than the derived cetane number of the base fuel composition by at least about 4.

13. A randomly branched nitrate composition comprising: a plurality of primary branched nitrate molecules having an empirical chemical formula of $C_nNO_3$, wherein $C_n$ is a branched aliphatic moiety which may be the same or different for each molecule, n is an integer selected from the group consisting of 8, 9, 10, 11 and 12, at least one carbon atom in the branched aliphatic moiety being bound to three or more carbon atoms, a branching index ranging from 1.8 to 2.2, and greater than 80% of the branches in the aliphatic moiety being in other than the alpha position.

14. The composition of clause 13, further comprising a plurality of branched nitrate molecules having an empirical chemical formula of $C_{n+1}NO_3$, wherein $C_{n+1}$ is a branched aliphatic moiety, n is an integer greater than or equal to eight, and at least one carbon atom in the branched aliphatic moiety is bound to three or more carbon atoms; and a plurality of primary branched nitrate molecules having an empirical chemical formula of $C_{n+1}NO_3$, wherein $C_{n+1}$ is a branched aliphatic moiety, n is an integer greater than or equal to eight, and at least one carbon atom in the branched aliphatic moiety is bound to three or more carbon atoms.

15. The composition as in any one of clauses 13-14, wherein the composition is characterized by a flash point of about 80° C. or greater or wherein the composition has a thermal decomposition temperature as measured by thermogravimetric analysis of greater than about 130° C.

16. The composition as in any one of clauses 13-15, wherein the composition has a nitrogen content of not more than about 7.5 wt. % with respect to the total weight of the composition.

17. A method of enhancing the ignition quality of an additized gasoline fuel compositions in each engine cycle comprising: providing an additized gasoline fuel composition comprising a base gasoline fuel composition, and a randomly branched nitrate composition comprising a plurality of primary nitrate molecules, each molecule therein having an empirical chemical formula of $C_nNO_3$, wherein $C_n$ is a branched aliphatic moiety which may be the same or different for each molecule, n is an integer selected from the group consisting of 8, 9, 10, 11 and 12, at least one carbon atom in the branched aliphatic moiety being bound to three or more carbon atoms, a branching index ranging from 1.8 to 2.2, and greater than 80% of the branches in the aliphatic moiety being in other than the alpha position; and injecting the additized gasoline fuel composition into the engine to enhance ignition quality.

Many alterations, modifications, and variations will be apparent to those skilled in the art in light of the foregoing description without departing from the spirit or scope of the present disclosure and that when numerical lower limits and numerical upper limits are listed herein, ranges from any lower limit to any upper limit are contemplated.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present invention. The invention illustratively disclosed herein suitably may be practiced in the absence of any element that is not specifically disclosed herein and/or any optional element disclosed herein.

The invention claimed is:

1. An additized fuel composition comprising:
a base fuel composition, and
a randomly branched nitrate composition comprising a plurality of primary nitrate molecules, each molecule therein having an empirical chemical formula of $C_nNO_3$, wherein $C_n$ is a branched aliphatic moiety which may be the same or different for each molecule, n is an integer selected from the group consisting of 8, 9, 10, 11 and 12, at least one carbon atom in the branched aliphatic moiety being bound to three or more carbon atoms, a branching index ranging from 1.8 to 2.2, and greater than 80% of the branches in the aliphatic moiety being in other than the alpha position; and
wherein the additized fuel composition is a diesel fuel composition or a gasoline fuel composition.

2. The fuel composition as in claim 1, wherein the additized fuel composition is a diesel fuel composition further comprising a biofuel.

3. The fuel composition as in claim 2, wherein the biofuel comprises a fatty acid methyl ester, a fatty acid ethyl ester, hydrotreated vegetable oil, or a blend thereof.

4. The fuel composition as in claim 1, wherein n is 9, 10, or 11.

5. The fuel composition as in claim 1, wherein the concentration of $C_nNO_3$ molecules in the randomly branched nitrate composition is at least about 60 wt. %.

6. The fuel composition as in claim 1, wherein the concentration of $C_nNO_3$ molecules in the randomly branched nitrate composition is at least about 60 wt. % and less than about 98 wt. %.

7. The fuel composition as in claim 1, wherein one of the carbon atoms bound to the at least one carbon atom in the branched aliphatic moiety is part of a methyl group.

8. The fuel composition as in claim 1, wherein the randomly branched nitrate composition is present at a concentration of about 500 ppmv to about 4000 ppmv.

9. The fuel composition as in claim 1, wherein when said additized fuel composition is combusted in the presence of oxygen, a lower mass of nitrogen oxide and nitrogen dioxide is produced than the mass of nitrogen oxide and nitrogen dioxide produced from the combustion of a fuel composition comprising the base fuel composition and a concentration of 2-ethylhexyl nitrate equal to the concentration of the randomly branched nitrate composition in the fuel composition.

10. The fuel composition as in claim 1, wherein the additized fuel composition is a diesel fuel composition and wherein after storage of the diesel fuel composition comprising about 1000 ppmv of the randomly branched nitrate composition for about six weeks at about 43° C., the diesel fuel composition comprises less than about 1.0 mg/100 mL of insoluble material as measured according to ASTM D4625-16e1.

11. The fuel composition as in claim 1, wherein the additized fuel composition is a gasoline fuel composition further comprising at least one oxygenate selected from the group consisting of di-isopropyl ether, C5 ether, C6 ether, ethanol, methanol, propanol, 2-propanol, butanol, 2-butanol, iso-butanol, tert-butanol, and mixtures thereof.

12. A method for making an additized fuel composition comprising:
providing a base fuel composition; and
adding a randomly branched nitrate composition to the base fuel composition to form an additized fuel composition, the randomly branched nitrate composition comprising a plurality of primary nitrate molecules, each primary nitrate molecule having an empirical chemical formula of $C_nNO_3$, wherein $C_n$ is a branched aliphatic moiety which may be the same or different for each molecule, n is an integer selected from the group consisting of 8, 9, 10, 11 and 12, at least one carbon atom in the branched aliphatic moiety being bound to three or more carbon atoms, a branching index ranging from 1.8 to 2.2, and greater than 80% of the branches in the aliphatic moiety being in other than the alpha position; and
wherein the additized fuel composition is a diesel fuel composition or a gasoline fuel composition.

13. The method of claim 12 further comprising providing the additized fuel composition to a gas station.

14. The method as in claim 12, wherein the additized fuel composition is a diesel fuel composition further comprising a biofuel.

15. The method as claim 14, wherein the biofuel comprises a fatty acid methyl ester, a fatty acid ethyl ester, hydrotreated vegetable oil, or a blend thereof.

16. The method as in claim 12, wherein n is 9, 10, or 11.

17. The method as in claim 12, wherein the concentration of $C_nNO_3$ molecules in the randomly branched nitrate composition is at least about 60 wt. %.

18. The method as in claim 12, wherein the concentration of $C_nNO_3$ molecules in the randomly branched nitrate composition is at least about 60 wt. % and less than about 98 wt. %.

19. The method as in claim 12, wherein substantially all the randomly branched nitrate molecules in the randomly branched nitrate composition have at least one carbon atom bound to three or more carbon atoms.

20. The method as in claim 12, wherein one of the carbon atoms bound to the at least one carbon atom in the branched is part of a methyl group.

21. The method as in claim 12, wherein the randomly branched nitrate composition is present in the fuel compositions at a concentration of about 100 ppmv to about 4000 ppmv.

22. The method as in claim 12, wherein the randomly branched nitrate composition is characterized by a flash point of about 80° C. or greater.

23. The method as in claim 12, wherein the additized fuel composition is a diesel fuel composition having a higher derived cetane number than the base diesel fuel composition.

24. The method as in claim 12, wherein the additized fuel composition is a diesel fuel composition having a derived cetane number greater than the derived cetane number of the base diesel fuel composition by at least about 4.

25. The method as in claim 12, wherein the additized fuel composition is a diesel fuel composition and wherein the diesel fuel composition has a higher derived cetane number than the base diesel fuel composition.

26. The method as in claim 12, wherein the additized fuel composition is a gasoline fuel composition having a lower anti-knock index than the base gasoline fuel composition.

27. The method as in claim 12, wherein the additized fuel composition is a gasoline fuel composition having an anti-knock index lower than the anti-knock index of the base gasoline fuel composition by at least about 3.

28. A randomly branched nitrate composition comprising:
a plurality of primary branched nitrate molecules having an empirical chemical formula of $C_nNO_3$, wherein $C_n$ is a branched aliphatic moiety which may be the same or different for each molecule, n is an integer selected from the group consisting of 8, 9, 10, 11 and 12, at least one carbon atom in the branched aliphatic moiety being bound to three or more carbon atoms, a branching index ranging from 1.8 to 2.2, and greater than 80% of the branches in the aliphatic moiety being in other than the alpha position.

29. The composition as in claim 28, wherein the composition is characterized by a flash point of about 80° C. or greater.

30. The composition as in claim 28, wherein the composition has a thermal decomposition temperature as measured by thermogravimetric analysis of greater than about 130° C.

31. The composition as in claim 28, wherein the composition has a nitrogen content of not more than about 7.5 wt. % with respect to the total weight of the composition.

32. The composition as in claim 28, wherein substantially all of the randomly branched nitrate molecules in the composition have at least one carbon atom bound to three or more carbon atoms.

33. A method of enhancing the ignition quality of an additized gasoline fuel compositions in each engine cycle comprising:
providing an additized gasoline fuel composition comprising a base gasoline fuel composition, and a randomly branched nitrate composition comprising a plurality of primary nitrate molecules, each molecule therein having an empirical chemical formula of $C_nNO_3$, wherein $C_n$ is a branched aliphatic moiety which may be the same or different for each molecule, n is an integer selected from the group consisting of 8, 9, 10, 11 and 12, at least one carbon atom in the branched aliphatic moiety being bound to three or more carbon atoms, a branching index ranging from 1.8 to 2.2, and greater than 80% of the branches in the aliphatic moiety being in other than the alpha position; and
injecting the additized gasoline fuel composition into the engine to enhance ignition quality.

* * * * *